(12) United States Patent
Majima et al.

(10) Patent No.: US 10,598,588 B2
(45) Date of Patent: Mar. 24, 2020

(54) SENSING METHOD AND SENSING SYSTEM

(71) Applicant: FUJIFILM Corporation, Tokyo (JP)

(72) Inventors: Wataru Majima, Minamiashigara (JP); Kazuhiro Oki, Minamiashigara (JP); Mitsuyoshi Ichihashi, Minamiashigara (JP)

(73) Assignee: FUJIFILM Corporation, Tokyo (JP)

( * ) Notice: Subject to any disclaimer, the term of this patent is extended or adjusted under 35 U.S.C. 154(b) by 3 days.

(21) Appl. No.: 15/790,350

(22) Filed: Oct. 23, 2017

(65) Prior Publication Data

US 2018/0047600 A1 Feb. 15, 2018

Related U.S. Application Data

(63) Continuation of application No. PCT/JP2016/062652, filed on Apr. 21, 2016.

(30) Foreign Application Priority Data

Apr. 24, 2015 (JP) .................. 2015-089607
Feb. 12, 2016 (JP) .................. 2016-025047
Apr. 8, 2016 (JP) .................. 2016-077841

(51) Int. Cl.
*G01N 21/21* (2006.01)
*G02B 5/30* (2006.01)
(Continued)

(52) U.S. Cl.
CPC ............ *G01N 21/21* (2013.01); *G01J 1/0429* (2013.01); *G01J 1/06* (2013.01); *G01N 21/23* (2013.01);
(Continued)

(58) Field of Classification Search
CPC ...... G01N 21/21; G01N 21/211; G01N 21/23; G01N 21/86; G01N 21/8609; G01N 21/88;
(Continued)

(56) References Cited

U.S. PATENT DOCUMENTS 5,059,023 A * 10/1991 Task .................. G01M 11/00
356/239.1
5,587,793 A 12/1996 Nakai et al.
(Continued)

FOREIGN PATENT DOCUMENTS

DE 102005030288 A1 1/2007
JP 50-26234 B1 8/1975
(Continued)

OTHER PUBLICATIONS

Extended European Search Report for corresponding Application No. 16783239.3, dated Feb. 23, 2018.
(Continued)

*Primary Examiner* — Gordon J Stock, Jr.
(74) *Attorney, Agent, or Firm* — Birch, Stewart, Kolasch & Birch, LLP

(57) ABSTRACT

A sensing method includes sensing the target object by sensing light that is derived from emitted light and has passed the target object, in which the emitted light is circularly polarized light, sensed light is circularly polarized light, and light derived from the emitted light is incident to the target object at an angle greater than 20° and equal to or smaller than 70° that is formed with a normal line of the target object.

11 Claims, 5 Drawing Sheets

(51) Int. Cl.
*G01V 8/10* (2006.01)
*G01N 21/86* (2006.01)
*G01N 21/23* (2006.01)
*G01J 1/04* (2006.01)
*G01J 1/06* (2006.01)

(52) U.S. Cl.
CPC ............. *G01N 21/86* (2013.01); *G01V 8/10* (2013.01); *G02B 5/30* (2013.01); *G02B 5/3033* (2013.01); *G01N 2021/216* (2013.01)

(58) Field of Classification Search
CPC .......... G01N 21/8803; G01N 21/8806; G01N 21/19; G01N 21/8422; G01N 2021/212; G01N 2021/213; G01N 2021/214; G01N 2021/215; G01N 2021/216; G01N 2021/217; G01N 2021/218; G01N 2021/8645; G01N 2021/869; G01N 21/95; G01N 21/9501; G01N 21/9505; G01N 21/9506; G01N 21/958; G01N 2021/9511; G01N 2021/9513; G01N 2021/9583; G01N 2021/9586; G01N 2021/8427; G01N 2021/8433; G01N 2021/8438; G01N 2021/8444; G01V 8/10; H01L 21/67288; G02B 5/30; G02B 5/3025; G02B 5/3033; G02B 5/3041; G02B 5/305; G02B 5/3083; G01J 3/447; G01J 2004/001; G01J 2004/002; G01J 4/00; G01J 4/02; G01J 4/04; G01J 1/0429; G01J 1/06; G01J 3/0224; G01J 2003/1291; G01B 11/0641; G01B 11/168; G07D 7/06; G07D 7/12; G07D 7/1205; G07D 7/121

See application file for complete search history.

(56) References Cited

U.S. PATENT DOCUMENTS

| | | | | |
|---|---|---|---|---|
| 8,437,002 B2* | 5/2013 | Horvath | ............. | G01B 11/0625 356/237.1 |
| 9,759,671 B2* | 9/2017 | Grubert | ................ | G01N 21/958 |
| 10,036,701 B2* | 7/2018 | Ichihashi | ................ | G02F 1/13 |
| 10,139,533 B2* | 11/2018 | Ichihashi | ............. | G02B 5/3016 |
| 2002/0084406 A1* | 7/2002 | Thawley | .................. | G07D 7/12 250/225 |
| 2003/0015673 A1* | 1/2003 | Luxem | .................. | G01N 21/21 250/559.09 |
| 2006/0082766 A1 | 4/2006 | Kim et al. | | |
| 2014/0029005 A1* | 1/2014 | Fiess | ..................... | G01N 21/21 356/364 |
| 2015/0109561 A1* | 4/2015 | Fuchida | ................ | G02B 1/105 349/96 |
| 2016/0054496 A1 | 2/2016 | Ichihashi et al. | | |
| 2016/0103015 A1 | 4/2016 | Ichihashi | | |
| 2016/0109630 A1* | 4/2016 | Ichihashi | ............. | C09K 19/54 250/338.1 |

FOREIGN PATENT DOCUMENTS

| | | |
|---|---|---|
| JP | 6-147986 A | 5/1994 |
| JP | 2008-58270 A | 3/2008 |
| JP | 2008-175940 A | 7/2008 |
| JP | 2011-149935 A | 8/2011 |
| JP | 2013-36888 A | 2/2013 |
| JP | 2015-25956 A | 2/2015 |
| WO | WO 2014/181799 A1 | 11/2014 |
| WO | WO 2014/203985 A1 | 12/2014 |

OTHER PUBLICATIONS

International Preliminary Report and Written Opinion of the International Searching Authority (Forms PCT/IB/326, PCT/IB/373 and PCT/ISA/237) for International Application No. PCT/JP2016/062652, dated Nov. 2, 2017, with English translation of the Written Opinion.
International Search Report (Form PCT/ISA/210) for International Application No. PCT/JP2016/062652, dated Jul. 26, 2016, with English translation.
Japanese Office Action, dated Sep. 4, 2018, for corresponding Japanese Application No. 2016-077841, with an English translation.
European Office Action, dated Jul. 25, 2019, for corresponding European Application No. 16783239.3.

* cited by examiner

SENSING METHOD AND SENSING SYSTEM

CROSS-REFERENCE TO RELATED APPLICATIONS

This application is a Continuation of PCT International Application No. PCT/JP2016/62652, filed on Apr. 21, 2016, which claims priority under 35 U.S.C. § 119(a) to Japanese Patent Application No. 2015-089607, filed on Apr. 24, 2015, Patent Application No. 2016-025047, filed on Feb. 12, 2016, and Patent Application No. 2016-077841, filed on Apr. 8, 2016. Each of the above application(s) is hereby expressly incorporated by reference, in its entirety, into the present application.

BACKGROUND OF THE INVENTION

1. Field of the Invention

The present invention relates to a sensing method and a sensing system. More specifically, the invention relates to a sensing method utilizing circularly polarized light and a sensing system.

2. Description of the Related Art

A method utilizing polarized light is known in the related art as a sensing method. In JP2008-58270A, for example, cracks on a silicon substrate are sensed with a system of irradiating the silicon substrate with polarized infrared light through a first linear polarizing filter and receiving reflected light or transmitted light from the silicon substrate through a second linear polarizing filter. This technology is acquired by using a phenomenon that the light intensity which can be sensed decreases, in a case where the reflected light or transmitted light of a portion without cracks is linearly polarized light and travels through the second linear polarizing filter, except for a case where specific conditions are satisfied, however, light which can be sensed is generated even in a case where the reflected light or transmitted light on the portion with cracks travels through the second linear polarizing filter due to diffuse reflection. In JP2013-36888A, a technology utilizing circularly polarized light in the technology of JP2008-58270A is disclosed.

WO 2014/181799 discloses a system of detecting foreign materials on a specular reflector, a transparent film, or a person as a target object, by using a film including a near infrared circularly polarized light separation layer and a visible light shielding layer.

SUMMARY OF THE INVENTION

In the system disclosed in JP2008-58270A, adjustment of a polarization direction using a first linear polarizing filter and a second linear polarizing filter is necessary to be performed, but in the sensing system disclosed in JP2013-36888A or WO 2014/181799, the adjustment described above is not necessary due to the usage of circularly polarized light. Here, WO 2014/181799 discloses the sensing of a target object using a transparent film, but does not disclose the sensing of a transparent product with further more excellent sensitivity.

An object of the invention is to provide a sensing method utilizing circularly polarized light, with higher sensitivity with decreased erroneous sensing, particularly, in a case where a transparent product is set as a target object and a sensing system.

In order to achieve the objects described above, the inventors have made intensive researches and found a new system. That is, the invention provides the following [1] to [15].

[1] A method of sensing a target object, including:
sensing the target object by sensing light that is derived from emitted light and has passed through the target object,
in which the emitted light is circularly polarized light,
the sensed light is circularly polarized light,
the target object is a transparent product, and
the light derived from the emitted light is incident to the target object at an angle greater than 20° and equal to or smaller than 70° that is formed with a normal line of the target object.

[2] The method according to [1],
in which the sensing is direct sensing of light which is the emitted light which has passed through the target object, and
a sense of circularly polarized light of the emitted light is opposite to a sense of circularly polarized light of the sensed light.

[3] The method according to [1],
in which the sensing is sensing of reflected light of light derived from the emitted light, and
a sense of circularly polarized light of the emitted light is the same as a sense of circularly polarized light of the sensed light.

[4] The method according to [3],
in which the sensing is sensing of reflected light which has passed through the target object again, after the emitted light passes through the target object and is reflected.

[5] The method according to any one of [1] to [4],
in which two or more emitted light rays having planes of incidence different from each other are used as the emitted light.

[6] The method according to [5],
in which the planes of incidence different from each other form an angle of 10° to 90°.

[7] The method according to [5] or [6],
in which three emitted light rays having planes of incidence different from each other are used as the emitted light.

[8] A system which senses a target object including:
an emission unit which selectively emits circularly polarized light;
a target object movement unit; and
a detection unit which selectively senses circularly polarized light, in a light path of the circularly polarized light in this order,
in which a sense of circularly polarized light selectively emitted by the emission unit is opposite to a sense of circularly polarized light selectively sensed by the detection unit,
a light path of light where light derived from the emitted light from the emission unit is incident to the detection unit intersects with the target object movement unit in an intersection portion, and
an angle formed by the light path and a normal line of the target object movement unit in the intersection portion is greater than 20° and equal to or smaller than 70°.

[9] The system according to [8],
in which the emission unit includes a light source and a circularly polarized light separation film 1,
the detection unit includes a circularly polarized light separation film 2 and a light receiving element,
the light source, the circularly polarized light separation film 1, the target object movement unit, the circularly polarized light separation film 2, and the light receiving element are disposed in a light path of the circularly polarized light in this order, and the circularly polarized light separation film 1 and the circularly polarized light separation film 2 allow selective transmission of circularly polarized light rays having senses opposite to each other.

[10] The system according to [9], in which both of the circularly polarized light separation film 1 and the circularly polarized light separation film 2 are films including circularly polarized light separation layers obtained by fixing a cholesteric liquid-crystalline phase.

[11] A system which senses a target object including:

an emission unit which selectively emits circularly polarized light;

a detection unit which selectively senses circularly polarized light;

a target object movement unit; and a mirror reflection member, in which the target object movement unit is included between the emission unit and the mirror reflection member and/or between the mirror reflection member and the detection unit, the emission unit and the detection unit are disposed at a position where the light derived from the emitted light from the emission unit is mirror-reflected by the mirror reflection member and incident to the detection unit, a sense of circularly polarized light selectively emitted by the emission unit is the same as a sense of circularly polarized light selectively sensed by the detection unit, a light path 1 of the light where light derived from the emitted light from the emission unit is incident to the mirror reflection member intersects with the target object movement unit in an intersection portion 1, an angle formed by the light path 1 and a normal line of the target object movement unit in the intersection portion 1 is greater than 20° and equal to or smaller than 70°, and/or a light path 2 of light where light derived from the emitted light from the emission unit is reflected by the mirror reflection member and sensed by the detection unit intersects with the target object movement unit in an intersection portion 2, and an angle formed by the light path 2 and a normal direction of the target object movement unit in the intersection portion 2 is greater than 20° and equal to or smaller than 70°.

[12] The system according to [8], in which the emission unit includes a light source and a circularly polarized light separation film 11, the detection unit includes a circularly polarized light separation film 12 and a light receiving element, the light source, the circularly polarized light separation film 11, and the mirror reflection member are included in the light path 1 in this order, the mirror reflection member, the circularly polarized light separation film 12, and the light receiving element are included in the light path 2 in this order, and the circularly polarized light separation film 11 and the circularly polarized light separation film 12 allow selective transmission of circularly polarized light rays having the same sense.

[13] The system according to [11] or [12], in which both of the circularly polarized light separation film 11 and the circularly polarized light separation film 12 are films including circularly polarized light separation layers obtained by fixing a cholesteric liquid-crystalline phase.

[14] The system according to any one of [8] to [13], in which two or more emission units with emitted light rays having planes of incidence different from each other are used as the emitted unit; and the detection units are respectively disposed in the planes of incidence.

[15] The system according to any one of [8] to [14],

In which the target object is a transparent product.

With the invention, a new method is provided as a sensing method utilizing circularly polarized light. It is possible to perform the sensing of a transparent product with high sensitivity and decreased erroneous sensing by using the method of the invention.

DESCRIPTION OF THE PREFERRED EMBODIMENTS

Figure 1A:
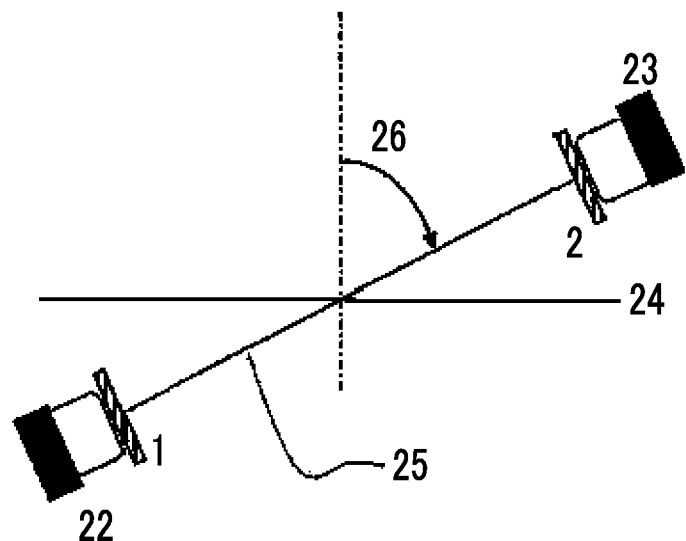
FIGS. 1A, 1B, 1C, and 1D are schematic views showing arrangement examples of a light source, a light, receiving element, and a circularly polarized light separation film for the sensing of a target object by using a method and a system of the invention with a plane of incidence of light, as sectional views.

Hereinafter, the invention will be described in detail.

A term "to" in this specification is used to include numerical values before and after the term as a lower limit value and an upper limit value.

In this specification, a term "(meth)acrylate" is used to include "any one or both of acrylate and methacrylate.

In this specification, values of angles (for example, an angle such as "90°") and relationships thereof (for example, "parallel" and "horizontal") include acceptable ranges of error in the technical fields of the invention. For example, this means that an error is within a range of less than ±10° of an exact angle. An error of an exact angle is preferably equal to or smaller than 5° and more preferably equal to or smaller than 3°.

In this specification, a term "sense" used in a case of describing circularly polarized light means the circularly polarized light is right circularly polarized light or left circularly polarized light. In a case where the light is seen so that the light travels towards the front side, the sense of the circularly polarized light is defined as right circularly polarized light, in a case where a distal end of an electric field vector rotates clockwise according to passage of time, and is defined as left circularly polarized light, in a case where the distal end thereof rotates counterclockwise.

In this specification, a term "selectively" used in a case of describing circularly polarized light means that the light intensity of circularly polarized light having any sense is greater than the light intensity of circularly polarized light having the other sense. Specifically, in a case of using the term "selectively", a degree of circular polarization of light is preferably equal to or greater than 0.3, more preferably equal to or greater than 0.6, and even more preferably equal to or greater than 0.8. The degree of circular polarization of light is substantially particularly preferably 1.0. Here, in a case where an intensity of a right circularly polarized light component of the light is set as $I_R$ and an intensity of a left circularly polarized light component is set as $I_L$, the degree of circular polarization is a value represented as $|I_R-I_L|/(I_R+I_L)$.

In this specification, the term "sense" may be used for a torsion direction of a spiral of a cholesteric liquid crystal. Regarding selective reflection of the cholesteric liquid crystal, right circularly polarized light is selectively reflected and left circularly polarized light is selectively transmitted, in a case where the torsion direction of the spiral of the cholesteric liquid crystal (sense) is right, and left circularly polarized light is selectively reflected and right circularly polarized light is selectively transmitted, in a case where the sense is left.

In this specification, the "plane of incidence" means a plane which is perpendicular to a plane of a target object (reflection plane) and includes an incidence ray, in a case where light (emitted light) is incident to a planar target object. The "plane of incidence" may further include a ray of mirror-reflected light and a ray of directly transmitted light of the emitted light.

In this specification, a term "birefringence" means retardation of a target object at a wavelength (luminescence peak) of emitted light. In a case where a target object is a film, a term "birefringence" includes in-plane retardation (Re) and retardation in a thickness direction (Rth) at a wavelength $\lambda$. The unit of both retardations is nm. Re at a specific wavelength of $\lambda$ nm is measured by emitting light at a wavelength of $\lambda$ nm in a film normal direction by using KOBRA 21ADH or WR (manufactured by Oji Scientific Instruments). The measurement can be performed by manually replacing a wavelength selection filter or converting a measured value by using a program or the like, at the time of selecting a measurement wavelength of $\lambda$ nm. In a case where the film to be measured is expressed with a uniaxial or biaxial refractive index ellipsoid, Rth is calculated by using the following method.

Rth at a specific wavelength of $\lambda$ nm is as follows. First, Re at a specific wavelength of $\lambda$ nm on six points is measured by emitting light at a wavelength of $\lambda$ nm in a film normal direction using an in-plane slow axis (determined by using KOBRA 21ADH or WR) as a tilted axis (rotation axis) (in a case where no slow axis is present, an arbitrary direction in the film plane is set as a rotation axis), from a direction tilted from one side of the normal direction by 10 degrees to 50°. Rth is calculated based on the measured retardation values, an assumed value of the average refractive index, and an input film thickness value by using KOBRA 21ADH or WR. As described above, in a case of a film having a direction where a value of retardation at a certain tilt angle is zero, by using the in-plane slow axis from the normal direction as a rotation axis, a sign of a retardation value at a tilt angle greater than the tilt angle described above is changed to minus and the value is calculated by KOBRA 21ADH or WR. The retardation values are measured in two arbitrarily tilted directions by using a slow axis as a tilted axis (rotation axis) (in a case where no slow axis is present, an arbitrary direction in the film plane is set as a rotation axis), and Rth can be calculated based on these values, an assumed value of average refractive index, and an input film thickness value by Expression (A) and Expression (B).

$$Re(\theta) = \left[ nx - \frac{(ny \times nz)}{\sqrt{\left\{ny\ \sin\left(\sin^{-1}\left(\frac{\sin(-\theta)}{nx}\right)\right)\right\}^2 + \left\{nz\ \cos\left(\sin^{-1}\left(\frac{\sin(-\theta)}{nx}\right)\right)\right\}^2}} \right] \times \frac{d}{\cos\left\{\sin^{-1}\left(\frac{\sin(-\theta)}{nx}\right)\right\}} \quad \text{Expression (A)}$$

Re ($\theta$) described above represents a retardation value in a direction tilted from the normal direction by an angle $\theta$. nx in Expression (A) represents a refractive index in a slow axis direction in the plane, ny represents a refractive index in a direction orthogonal to nx in the plane, and nz represents a refractive index in a direction orthogonal to nx and ny. d represents a film thickness.

$$Rth = ((nx+ny)/2 - nz) \times d \quad \text{Expression (B)}$$

In this specification, light may be infrared light, visible light, ultraviolet light, or light in a wavelength range included in a wavelength range of infrared light and visible light, a wavelength range of visible light and ultraviolet light, or a wavelength range of infrared light, visible light, and ultraviolet light. The light may be light having a specific wavelength width of 1 nm, 10 nm, 50 nm, 100 nm, 150 nm, or 200 nm. The wavelength width is preferably equal to or greater than 50 nm.

Visible light is light having wavelengths which are visually recognizable by a person among electromagnetic waves and indicates light in a wavelength range of 380 nm to 780 nm. Infrared light (infrared light beam) is electromagnetic waves in a wavelength range which is longer than that of visible light and shorter than radiowaves. Near infrared light is electromagnetic waves in a wavelength range of 780 nm to 2500 nm. Ultraviolet light is electromagnetic waves in a wavelength range which is shorter than that of visible light and longer than that of X rays. The ultraviolet light may be light in a wavelength range that is distinguished from those of visible light and X rays, and is, for example, light in a range of a wavelength of 10 to 380 nm.

In the method of the invention, near infrared light is preferably used as the emitted light. In a case of using near infrared light as the emitted light, the wavelength range thereof is preferably 780 nm to 1,500 nm or 800 nm to 1,500 nm. In general, light in a wavelength range corresponding to a wavelength range of near infrared light which is used in an infrared camera, an infrared photoelectric sensor, infrared communication, or the like may be used. As the emitted light, two kinds of light rays, that is, two light rays in different wavelength ranges may be used.

In this specification, a term "reflected light" has a meaning including mirror-reflected light (directly reflected light) and diffuse reflected light (scattered light). A term "transmitted light" has a meaning including scattered transmitted light, directly transmitted light, and diffracted light.

In this specification, a term "light path" means a path of light from the emission unit to the detection unit or a part thereof. In the description of the system, a "light path 1 of the light where light derived from the emitted light from the emission unit is incident to the mirror reflection member" means a straight line connecting the emission unit (more specifically, the center of the light source) and a position where the light derived from the emitted light from the emission unit is incident to the mirror reflection member. A "light path 2 of light where light derived from the emitted light from the emission unit is reflected by the mirror reflection member and sensed by the detection unit" means a straight line connecting the position where the light derived from the emitted light from the emission unit is incident to the mirror reflection member, and the detection unit (more specifically, the center of the light receiving element). The light path is shown as a straight line in drawings or the like, but this does not mean that emitted light and sensed light are limited to light having high directivity.

In this specification, the "light derived from the emitted light" means light derived from the emitted light excluding ambient light of the method or the system of the invention, and means emitted light, light obtained by allowing the emitted light to be transmitted through a target object, light obtained by allowing reflection of the emitted light, light obtained by allowing reflection of the light which is obtained by allowing the emitted light to be transmitted through a target object, or light obtained by further allowing the light which is obtained by reflection of the light which is obtained by allowing the emitted light to be transmitted through a target object, to be transmitted through a target object.

In the sensing method of the invention, polarized light is used as light. By using polarized light, light derived from the emitted light from the emission unit can be dominantly sensed, compared to surrounding light and an S/N ratio can be increased. In addition, it is possible to sense a transparent target object. In addition, in the invention, circularly polarized light is used as the polarized light. In a case where light transmitted through a target object is sensed by using circularly polarized light, it is easy or unnecessary to adjust an azimuth of a film used for the sensing of polarized light, unlike in a case of using linearly polarized light as the polarized light.

A polarized state of light can be measured using a spectral radiance meter or a spectrometer mounted on a circularly polarizing plate. In this case, the intensity of light measured through a right circularly polarizing plate corresponds to $I_R$ and the intensity of light measured through a left circularly polarizing plate corresponds to $I_L$. The measurement can also be performed by attaching the circularly polarizing plate to an illuminometer or a spectrometer. A ratio can be measured by measuring the right circularly polarized light intensity by attaching a right circularly polarizing transmission plate and measuring the left circularly polarized light intensity by attaching a left circularly polarizing transmission plate.

<Target Object>

A target object to be sensed by the method of the invention is a transparent product. In this specification, a term "transparency" means a state where natural light in a wavelength range of the light used is transmitted. The wavelength range of the light used may be a wavelength range of the emitted light. Light transmittance of the light may be equal to or greater than 50%, equal to or greater than 60%, equal to or greater than 80%, equal to or greater than 90%, or equal to or greater than 95%. The light transmittance used as a scale of transparency can be calculated by using a method disclosed in JIS-K7105, that is, by measuring total light transmittance and scattered light quantity with an integrating sphere type light transmittance measuring device and subtracting diffuse transmittance from the total light transmittance. In this specification, in a case of a transparent product, the transparent product is preferably a product through which natural light in a wavelength range of the light used is transmitted, and at the same time, natural light in a visible light range is transmitted. For example, light transmittance in the visible light range may be equal to or greater than 80% or equal to or greater than 85%.

The transparent product may include entirely transparent surfaces in all directions, or may include partially opaque portions. For example, opaque portions having a surface area of equal to or smaller than 70%, equal to or smaller than 60%, equal to or smaller than 50%, equal to or smaller than 40%, equal to or smaller than 30%, equal to or smaller than 20%, equal to or smaller than 10%, or equal to or smaller than 5% with respect to a surface area of a film-shaped transparent product may be included.

The target object to be sensed by the method of the invention may have a flat surface shape or a shape similar to the flat surface. The target objects may be aggregated to form a flat surface shape, at the time of the sensing, or the target object may move in parallel to the flat surface so as to become similar to the flat surface shape, at the time of the sensing. Examples of the target object include a film, a sheet, and a plate. Specific examples thereof include a card, paper, and a plastic film (an optical film or a transparent film for packaging).

The target object to be sensed by the method of the invention may have birefringence in any direction. In this specification, the expression "having birefringence" means that Re or Rth is equal to or greater than 20 nm, in a case of a film or a plate-like product, for example, and Re or Rth is preferably equal to or greater than 50 nm, more preferably equal to or greater than 100 nm, and even more preferably equal to or greater than 200 nm. A polarization state of emitted circularly polarized light changes due to birefringence of a target object and light intensity to be sensed in the detection unit increases. Thus, the target object can be sensed. The target object sensed by the method of the invention preferably has birefringence in a direction in which emitted light is incident and travels in the method of the invention.

In the method of the invention, in a case where a film having high birefringence is set as a target object, it is possible to perform the sensing with high sensitivity, and in a case where a film having low birefringence is set as a target object, it is also possible to perform the sensing with high sensitivity.

Examples of the film having low birefringence include an acryl film (for example, TECHNOLLOY Film S000 manufactured by Escarbo Sheet Co., Ltd, and the like), an acryl plate (for example, TECHNOLLOY Sheet manufactured by ESCARBO, CLAREX Precision Sheet manufactured by Nitto Jushi Kogyo Co., Ltd., and the like), a polycarbonate film (for example, TECHNOLLOY Film C000 manufactured by ESCARBO, and the like), glass (for example, synthetic quartz glass manufactured by Asahi Glass Co., Ltd, and the like), and a TAC (triacetylcellulose) film (for example, Fujitac manufactured by FUJIFILM Corporation).

<Sensing Method>

In a sensing method of the invention, circularly polarized light is used as described above. The sensing of a target object is performed by sensing light which is derived from light emitted to a target object and is transmitted through the target object. In the sensing method of the invention, in a state where there is no target object, light derived from the emitted light from the emission unit is not sensed in the detection unit or in a state with low light intensity. This can be achieved by adjusting a sense of circularly polarized light of the emitted light and a sense of circularly polarized light to be sensed as will be described later. In addition, in the method of the invention, light intensity sensed due to the transmission of light derived from the emitted light through a target object in the state described above increases, and thus, a target object is sensed. That is, a polarization state of the light transmitted through a target object changes due to birefringence of a target object and contains circularly polarized light having a sense opposite to that of the circularly polarized light before the transmission. Thus, light intensity to be sensed in the emission unit is increased by using this.

Regarding an increase in light intensity at this time, the light intensity may be, for example, equal to or greater than 200%, equal to or greater than 300%, or equal to or greater than 500% with respect to light intensity in a state where at target object is not present.

The kind of a target object may be determined with an amount of change in light intensity. For example, a transparent product and an opaque product, or a plurality of products having different transparency or birefringence may be distinguished from each other. In this case, the target object to be determined may include an opaque product. In a case where an opaque product is introduced to a light path, not only light from the emission unit, but ambient light is not sensed, either, and therefore, light intensity to be sensed in the detection unit decreases. Accordingly, an opaque product sensed to be distinguished from a transparent product may be sensed due to a decrease in light intensity sensed by a target object.

In the sensing method of the invention, the emitted light is incident to a target object so as to form an angle greater than 20° and equal to or smaller than 70° with a normal line of a target object. A birefringence (retardation) of a substance increases, as a thickness thereof increases. Accordingly, by allowing light to be incident to a target object so as to form the angle described above, it is possible to increase a distance by which the light passes through a target object, substantially increase a thickness, and increase birefringence. In a case where a target object is a film having a small Re which is, for example, approximately 0 to 100 nm and Rth which is greater than Re, it is possible to increase light intensity of circularly polarized light to be sensed, by setting incidence ray to form an angle with a normal line of a target object.

Accordingly, in the system of the invention, for example, a film material having low birefringence can also be sensed with excellent sensitivity.

The angle described above is preferably 25° to 65° and more preferably 30° to 62°.

In this specification, a normal line of a target object means a normal line extending from an emitted light incident position of a target object on an emitted light incidence side with respect to a target object. In a case where a target object has a shape similar to a planar shape, the normal line means a normal line based on the similar plate.

In the sensing method of the invention, two or more emitted light rays may be used or three or more emitted light rays are more preferably used. Two or more emitted light rays may be emitted light rays in different wavelength ranges, may be emitted light rays having different angles formed with a normal line of a target object, or may be emitted light rays having different planes of incidence. The two or more emitted light rays may be emitted light rays having different two or more points among these points.

Light intensity of circularly polarized light to be sensed may be added by using the two or more emitted light rays and used in the sensing, or light intensity of circularly polarized light to be sensed may be used in the sensing based on emitted light having higher sensitivity (greater S/N). It is preferable that the sensing is performed based on emitted light having high sensitivity (greater S/N).

By using emitted light rays incident to a target object from different planes of incidence, it is possible to increase sensitivity of the sensing of a target object having birefringence in which a slow axis direction is unclear. The emitted light is emitted from a direction in which birefringence is small in a target object, and thus, it is possible to prevent a decrease in sensitivity.

In a case where the two or more emitted light rays incident to a target object from different planes of incidence are used, an angle formed by two planes of incidence of the arbitrary two emitted light rays among these emitted light rays is preferably 10° to 90°, more preferably 30° to 90°, and even more preferably 45° to 90°. An angle formed by incidence directions of arbitrary two emitted light rays among these emitted light rays (angle obtained by setting a normal line as a center, in a case of being seen in a normal direction of a target object) is preferably 10° to 170°, more preferably 30° to 150°, and even more preferably 45° to 135°. In a case of emitted light rays incident to a target object from planes of incidence different from each other, three or more emitted light rays are preferably used, and three emitted light rays are particularly preferably used.

A sensing method using two or more emitted light rays can be performed, for example, by using a sensing system including two or more emission units which will be described later.

The adjustment of the sense of the circularly polarized light of the emitted light and the sense of the circularly polarized light to be sensed described above can be performed, for example, as follows.

In a first aspect (transmission type), the direct sensing of light of the emitted light transmitted through a target object is performed, and a sense of circularly polarized light selectively contained in the emitted light and a sense of circularly polarized light selectively contained in the light to be sensed are set to be opposite to each other. The direct sensing of light means the sensing of transmitted light of a target object, particularly, directly transmitted light. In the direct sensing of light, the light derived from the emitted light may not be reflected until the sensing, and the light transmitted through a target object may be sensed as it is.

In a second aspect (reflective type), the sensing of reflected light of the light derived from the emitted light is performed, and a sense of circularly polarized light selectively contained in the emitted light and a sense of circularly polarized light selectively contained in the light to be sensed are set to be the same as each other. At this time, the reflected light is preferably mirror-reflected light. In the second aspect, the light derived from the emitted light may be transmitted through a target object before the reflection, may be transmitted through a target object after the reflection, or may be transmitted through a target object before and after the reflection. Among these, particularly the light is preferably transmitted before and after the reflection. That is, the sensing is preferably the sensing is sensing of reflected light which has passed through the target object again, after the emitted light passes through the target object and is reflected. The light is transmitted through a target object twice, and thus, it is possible to increase sensitivity of the sensing.

<Sensing System>

In order to realize the method of the invention, the system of the invention can be used, for example. The system of the invention may be a device at least including an emission unit, a target object movement unit, and a detection unit, or may have a combination including a target object movement unit, an emission unit, and a detection unit.

In one aspect (transmission type), the system includes an emission unit which selectively emits circularly polarized light, a target object movement unit, and a detection unit which senses circularly polarized light, in a light path of circularly polarized light in this order. At this time, the detection unit is at a position where light emitted from the emission unit is incident, the light path of light where light emitted from the emission unit is incident to the detection unit intersects with the target object movement unit, and the sense of the circularly polarized light selectively emitted by the emission unit and the sense of the circularly polarized light selectively sensed by the detection unit are opposite to each other.

In another aspect (reflective type), the system includes an emission unit which selectively emits circularly polarized light, a detection unit which selectively senses circularly polarized light, a target object movement unit, and a mirror reflection member. At this time, the target object movement unit is disposed between the emission unit and the mirror reflection member or between the mirror reflection member and the detection unit, and the target object movement unit is disposed between the emission unit and the mirror reflection member and between the mirror reflection member and the detection unit. The emission unit and the detection unit are at a position where the light emitted from the emission unit is mirror-reflected by the mirror reflection member and incident to the detection unit. The light path 1 of light where the light derived from the emitted light from the emission unit is incident to the mirror reflection member intersects with the target object movement unit in the intersection portion 1, the light path 2 of light where the light derived from the emitted light from the emission unit is reflected by the mirror reflection member and sensed by the detection unit intersects with the target object movement unit in the intersection portion 2, or the light path 1 of light where the light derived from the emitted light from the emission unit is incident to the mirror reflection member intersects with the target object movement unit in the intersection portion 1, and the light path 2 of light where the light derived from the emitted light from the emission unit is reflected by the mirror reflection member and sensed by the detection unit intersects with the target object movement unit in the intersection portion 2. The sense of the circularly polarized light selectively emitted by the emission unit and the sense of the circularly polarized light selectively sensed by the detection unit are the same as each other.

In both aspects, it is preferable that the detection unit is in the planes of incidence of light emitted from the emission unit.

As will be described later, the emission unit preferably includes a light source and a circularly polarized light separation film, and the detection unit preferably includes a light receiving element and a circularly polarized light separation film. FIGS. 1A to 1D show arrangement examples of the light source, the light receiving element, and the circularly polarized light separation film for sensing the target object.

In arrangements A, B, C, and D which are the aspect of the transmission type, a light source 22, a circularly polarized light separation film on a light source side (in this specification, may be referred to as a circularly polarized light separation film 1), a target object movement unit 24, a circularly polarized light separation film on a light receiving element side (in this specification, may be referred to as a circularly polarized light separation film 2), and a light receiving element 23 are arranged in a light path of circularly polarized light in this order. The circularly polarized light separation film 1 and the circularly polarized light separation film 2 selectively transmit circularly polarized light having senses opposite to each other, and in a case where a target object is not present, most of light from the light source is not directly sensed by the light receiving element. In a case where a target object is disposed in an intersection portion of the light path and the target object movement unit, light intensity of light to be sensed in the light receiving element increases and a target object is sensed due to the increase thereof.

The arrangement C which is the aspect of the reflective type has a configuration in which reflected light is sensed by using the mirror reflection member 16. That is, a circularly polarized light separation film 11 selectively transmits circularly polarized light having the same sense as that of a circularly polarized light separation film 12, and in a case where a target object is not present, most of light from the light source is not sensed by the light receiving element. In a case where a target object is disposed in the intersection portion 1 and/or the intersection portion 2, light intensity of light to be sensed in the light receiving element increases and a target object is sensed due to the increase thereof.

In the arrangement C, the light source and the light receiving element are arranged on the same side surface side of the circularly polarized light separation film as seen from the target object. In this configuration, a layer which shields light (particularly light at a wavelength in an emitted light range) may be provided between the light receiving element and the light source, so that the light receiving element is not affected by the direct light from the light source.

In the system of the invention of the aspect of the transmission type, in an intersection portion where the light path of light where the light derived from the emitted light from the emission unit is incident to the detection unit, and the target object movement unit intersects with each other, an angle (tilt angle 26 shown in FIGS. 1A, 1B, and 1D) formed by the light path and a normal line of the target object movement unit is greater than 20° and equal to or smaller than 70°. The angle is preferably 25° to 65° and more preferably 30° to 62°.

In the system of the invention of the aspect of the reflective type, at least any one of an angle (tilt angle 26-1 shown in FIG. 1C) formed by the light path 1 and a normal direction of the target object movement unit in the intersection portion 1, and an angle (tilt angle 26-2 shown in FIG. 1C) formed by the light path 2 and a normal line of the target object movement unit in the intersection portion 2 is greater than 20° and equal to or smaller than 70°, or both of the angle (tilt angle 26-1 shown in FIG. 1C) formed by the light path 1 and a normal direction of the target object movement unit in the intersection portion 1, and the angle (tilt angle 26-2 shown in FIG. 1C) formed by the light path 2 and a normal line of the target object movement unit in the intersection portion 2 are preferably greater than 20° and equal to or smaller than 70°. Both angles are preferably 25° to 65° and more preferably 30° to 62°.

In the system of the invention, a housing may be provided so as to shield light for the target object movement unit. For example, a housing can be provided as shown in the arrangements B and D. At this time, as shown in the arrangement B, the circularly polarized light separation film may be provided on a window part of the housing. At this time, a straight line connecting the centers of two window parts of the housing is a normal line of the target object movement unit may intersect with each other by an angle greater than 20° and equal to or smaller than 70°. As shown in the arrangement D, an attachment for shielding light (particularly light at a wavelength in an emitted light range) may be provided in any one or both of a portion between the window part and the emission unit and a portion between the window part and the detection unit, so that an effect of ambient light is more hardly received.

In the system of the invention of the aspect of the reflective type, a layer which shields light (particularly light at a wavelength in an emitted light range) may be provided between the emission unit and the detection unit, so that the detection unit does not receive an effect of direct light from the emission unit.

[Target Object Movement Unit]

The target object movement unit means a portion where a target object to be sensed can be disposed, and includes a portion where a target object can be held in a plane. In the system of the invention, a target object may be sensed in this portion. For example, in the arrangements A, B, and D of FIGS. 1A to 1D, the target objects may continuously move in a horizontal direction as a straight line shown in the drawings, may continuously move back and forth of the space, or may be simply disposed in a straight line portion shown in the drawings. The target object in the arrangement C may move in a vertical direction of the space as a straight line shown in the drawings, may move back and forth of the space, or may be simply disposed in a straight line portion shown in the drawings.

In this specification, an expression "movement" of the target object may mean movement in one direction, reciprocating, or non-continuous movement including disposition and removal.

In this specification, the normal line of the target object movement unit means a normal line of the target object movement unit extending from an emitted light incidence position of the target object movement unit on an emitted light incidence side with respect to a portion where a target object can be held in a plane, and means a normal line with respect to a plane of a target object which can be held, in the target object movement unit. As an example of the target object movement unit, a film transportation unit or the like is used.

As a specific example of the sensing system, a system which confirms the passage of a product in a production line of a factory is used. Examples of the product include an optical film, a packaging film, an acryl film, and an acryl plate.

[Emission Unit]

The emission unit selectively emits circularly polarized light in a wavelength range of specific light. The wavelength range of the emitted light may be selected in accordance with a target object. The emission unit includes a light source. In addition, the emission unit preferably includes a light source and a circularly polarized light separation film. In a case where the light source is a light source which emits linearly polarized light, the emission unit may include a light source and a phase difference film such as a λ/4 phase difference layer.

As the light source, any light source can be used as long as it emits light at a photosensitive wavelength of the light receiving element, such as a halogen lamp, a tungsten lamp, an LED, an LD, a xenon lamp, or a metal halide lamp, and an LED or an LD are preferable, from the viewpoints of a small size, emission directivity, monochromatic light, and pulse modification ability.

The emission unit preferably has, for example, a configuration in which the light source is included in a housing, the circularly polarized light separation film is arranged in a light emission portion, and the light other than light passing through the circularly polarized light separation film is not emitted from the light source. In a case where the circularly polarized light separation layer includes the linearly polarized light separation layer and the λ/4 phase difference layer, it is preferable that the λ/4 phase difference layer is disposed on the outer side and the linearly polarized light separation layer is disposed on the light source side.

The system of the invention may include two or more emission units. For example, two or more emission units may be included so as to provide emitted light rays having different planes of incidence, two or more emission units may be included so as to provide emitted light rays having different angles formed by a normal line of a target object on the same plane of incidence, or two or more emission units may be included so as to provide emitted light rays having different planes of incidence and angles formed by a normal line of a target object. Among these, it is preferable that two or more emission units may be included so as to provide emitted light rays having different planes of incidence.

In addition, the system of the invention may include two or more kinds of emission units in different wavelength ranges of emitted light.

[Detection Unit]

The detection unit may selectively sense circularly polarized light in a wavelength range of the light emitted from the emission unit.

The detection unit may be, for example, formed of a light receiving element and a circularly polarized light separation film.

Examples of the light receiving element include a photodiode type sensor using a semiconductor such as Si, Ge, HgCdTe, PtSi, InSb, or PbS, a detector in which light detecting elements are linearly arranged, or a CCD (charge coupled device) or a CMOS (complementary metal oxide semiconductor) for acquiring an image.

The detection unit is preferably a light intensity sensing unit capable of measuring light intensity.

As a component of the detection unit, the circularly polarized light separation film may be used by being bonding to the light receiving element which can sense light at wavelengths at which the circularly polarized light separation film selectively transmits any one of the right circularly polarized light and the left circularly polarized light. The circularly polarized light separation film may be disposed on the light receiving surface of the light receiving element.

The sensor preferably has a configuration in which the light receiving element is in a housing, the circularly polarized light separation film is arranged in a light receiving portion, and the light other than light passed through the circularly polarized light separation film does not approach the light receiving element. In a case where the circularly polarized light separation film includes a linearly polarized light separation layer which will be described later and a λ/4 phase difference layer, it is preferable that the λ/4 phase difference layer is disposed on the outer side and the linearly polarized light separation layer is disposed on the light receiving element side.

Figure 4:
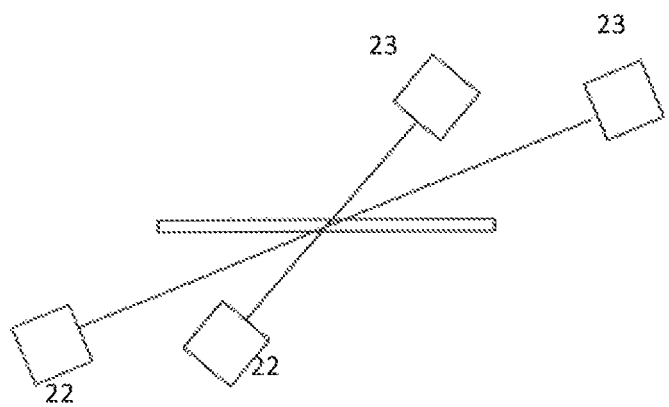
FIGS. 4 and 5 are schematic views showing arrangement examples of a plurality of light sources and a plurality of light receiving elements.
Figure 5:
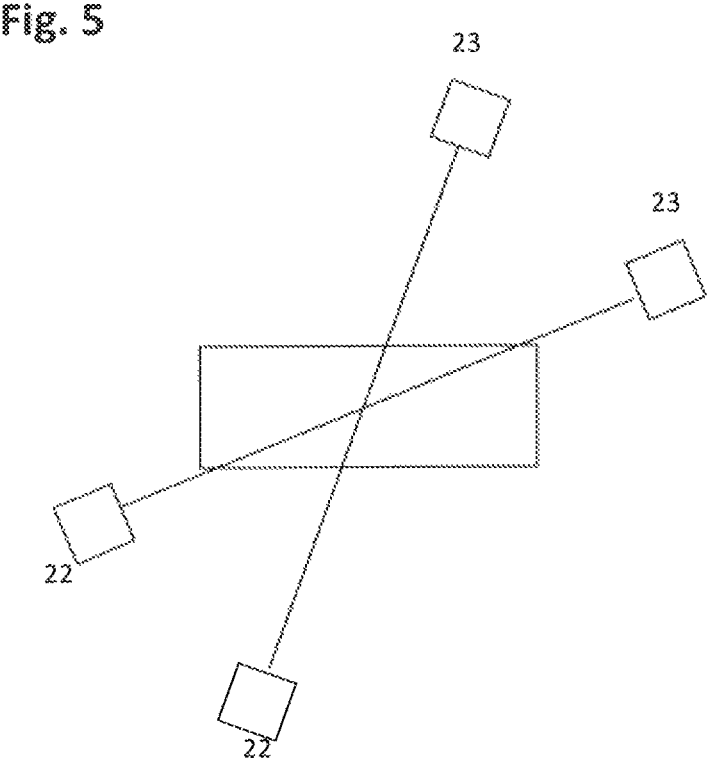

The system of the invention may include two or more detection units (See FIGS. 4 and 5). Particularly, in a case where the system includes two or more emission units, it is preferable that two or more detection units which detect light derived from each emission unit are included. It is preferable that the detection units which detect light derived from each emission unit are respectively disposed in the planes of incidence of the emitted light of each emission unit.

In a case where the system of the invention includes two or more kinds of emission units in different wavelength ranges of the emitted light, it is preferable that a detection unit including a light receiving element capable of detecting light in each wavelength range is included.

[Circularly Polarized Light Separation Film]

The circularly polarized light separation film is a film which selectively allows the transmission of any one of right circularly polarized light and left circularly polarized light in a specific wavelength range. It is preferable that the circularly polarized light separation film separates specific light (natural light or unpolarized light) which is incident from one side surface into right circularly polarized light and left circularly polarized light and selectively allows the transmission of any one thereof to the other side surface. At that time, the other circularly polarized light may be reflected or absorbed.

The circularly polarized light separation film may selectively allow the transmission of any one of right circularly polarized light and left circularly polarized light with respect to the light incident from any surface, or may selectively allow the transmission of any one of right circularly polarized light and left circularly polarized light with respect to only the light incident from one surface and may not allow the same selective transmission with respect to the light incident from the other side surface. When using the latter case, the arrangement for acquiring desirable circularly polarized light selectivity may be used. In addition, the circularly polarized light separation film may separate light incident from any surface into right circularly polarized light and left circularly polarized light and selectively allow the transmission of any one thereof to the other side surface, or may separate only the light incident from any one surface into right circularly polarized light and left circularly polarized light, selectively allow the transmission of any one thereof to the other side surface, and may not allow the circularly polarized light separation with respect to the light incident from the other side surface. When using the latter case, the arrangement for acquiring desirable circularly polarized light selectivity may be used.

Regarding the circularly polarized light separation film, light transmittance {(light intensity of transmitted circularly polarized light)/(light intensity of incident circularly polarized light)×100} of the circularly polarized light having the same sense as the incidence ray when any one of the right circularly polarized light and left circularly polarized light in a specific wavelength range having a width equal to or greater than 50 nm is incident, may be 70% or more, 80% or more, 90% or more, 95% or more, 99% or more, or substantially preferably 100%. At that time, light transmittance {(light intensity of transmitted circularly polarized light)/(light intensity of incident circularly polarized light)× 100} of the circularly polarized light having the same sense as the incidence ray when the circularly polarized light having the other sense is incident in the same wavelength range described above, may be 30% or less, 20% or less, 10% or less, 5% or less, 1% or less, or substantially preferably 0%.

(Circularly Polarized Light Separation Layer)

The circularly polarized light separation film includes a circularly polarized light separation layer which selectively allows the transmission of any one of right circularly polarized light and left circularly polarized light in a specific wavelength range. In addition, in this specification, the circularly polarized light separation layer used on the light source side may be referred to as a circularly polarized light separation layer 1 and the circularly polarized light separation layer used on the light receiving element side may be referred to as a circularly polarized light separation layer 2.

A wavelength bandwidth of the wavelength range in which the circularly polarized light separation layer selectively allows the transmission of any one of right circularly polarized light and left circularly polarized light may be equal to or greater than 5 nm, equal to or greater than 10 nm, equal to or greater than 20 nm, equal to or greater than 30 nm, equal to or greater than 40 nm, or equal to or greater than 50 nm. The specific wavelength range in which the circularly polarized light separation layer selectively allows the transmission of any one of right circularly polarized light and left circularly polarized light may include wavelengths of light necessary for the sensing of the target object in accordance with the usage state of the circularly polarized light separation film, and may be 50% or more, 60% or more, 70% or more, 80% or more, or 90% or more of the wavelength range of 800 nm to 1500 nm, and substantially 100% thereof.

The circularly polarized light separation layer may selectively allow the transmission, reflection, or absorption of light outside of the wavelength range in which any one of the right circularly polarized light and the left circularly polarized light is selectively transmitted. In addition, the circularly polarized light separation layer may selectively allow the transmission of any one of right circularly polarized light and left circularly polarized light, and may reflect or absorb the other circularly polarized light.

As the circularly polarized light separation layer, a layer obtained by fixing a cholesteric liquid-crystalline phase or a layer formed of a laminate including a linearly polarized light separation layer and a λ/4 phase difference layer can be used, for example.

(Reflected Light Scattering Circularly Polarized Light Separation Layer and Reflected Light Non-Scattering Circularly Polarized Light Separation Layer)

The circularly polarized light separation film may include a reflected light scattering circularly polarized light separation layer. The reflected light scattering circularly polarized light separation layer has greater diffuse reflectance/specular reflectance of circularly polarized light having another sense, than scattering transmittance/straight transmittance of the circularly polarized light selectively transmitting at a specific wavelength. In this specification, the circularly polarized light separation film including the reflected light scattering circularly polarized light separation layer may be referred to as a scattering type circularly polarized light separation film and the circularly polarized light separation film not including the reflected light scattering circularly polarized light separation layer may be referred to as a mirror type circularly polarized light separation film.

The values of scattering transmittance/straight transmittance and diffuse reflectance/specular reflectance are respectively values calculated based on values measured by using a spectrophotometer and an integrating sphere unit. The straight transmittance and specular reflectance can be measured with a spectrophotometer and total angle measurement values of transmittance and reflectance can be measured by incorporating an integrating sphere unit into a spectrophotometer. The straight transmittance is a measurement value at an incidence angle of 0° and the specular reflectance may be, for example, a measurement value at an incidence angle of 5° for convenience of the measurement. The scattering transmittance can be calculated by subtracting the straight transmittance from the total angle measurement values of transmittance and the diffuse reflectance can be calculated by subtracting the specular reflectance from the total angle measurement values of reflectance. A filter which functions as a circularly polarized light filter at a measurement wavelength may be installed on the light source side, in order to measure straight transmittance, specular reflectance, and total angle measurement values of transmittance and reflectance of any one circularly polarized light.

The reflected light scattering circularly polarized light separation layer may be formed of a layer obtained by fixing a cholesteric liquid-crystalline phase, and the specific wavelength described above is a center wavelength of the circularly polarized light reflection (selective reflection) of a layer obtained by fixing a cholesteric liquid-crystalline phase which will be described later. The reflected light scattering circularly polarized light separation layer has great scattering properties of reflected light and transmitted light with respect to the circularly polarized light at a specific wavelength (selective reflection wavelength) of one sense. Meanwhile, reflected light scattering circularly polarized light separation layer has low scattering properties with respect to the circularly polarized light having the opposite sense. That is, in a case where the reflected light scattering circularly polarized light separation layer is formed of right helical cholesteric liquid crystal, for example, scattering properties of reflected circularly polarized light and transmitted circularly polarized light with respect to right circularly polarized light at the selective reflection wavelength are great and on the other hand, the scattering properties thereof with respect to left circularly polarized light may be low. In a case where the reflected light scattering circularly polarized light separation layer is formed of left helical cholesteric liquid crystal, for example, scattering properties of reflected circularly polarized light and transmitted circularly polarized light with respect to left circularly polarized light at the selective reflection wavelength are great and the scattering properties thereof with respect to right circularly polarized light may be low.

Regarding the reflected light scattering circularly polarized light separation layer, a value of scattering transmittance/straight transmittance of circularly polarized light having the sense described above at the specific wavelength is 0.00 to 0.10 and may be preferably 0.00 to 0.05. With such values, it is possible to ensure high light intensity and degree of circular polarization in a specific light path. In addition, regarding the circularly polarized light separation layer, a value of diffuse reflectance/specular reflectance of circularly polarized light having the sense opposite to the sense selectively transmitted at the specific wavelength is 2.0 to 7.5 and may be preferably 3.0 to 5.0. In a case where the value of diffuse reflectance/specular reflectance is equal to or smaller than 7.5, it is possible to prevent a decrease in transparency of the circularly polarized light separation layer.

In addition, regarding the reflected light scattering circularly polarized light separation layer, a haze value measured with natural light at the specific wavelength described above is greater than 10 and equal to or smaller than 55 and may be preferably greater than 20 and equal to or smaller than 50. Here, the haze value is calculated as a value of {(scattering transmittance of natural light)/(scattering transmittance of natural light+straight transmittance of natural light)× 100(%)}. The haze value can be calculated based on values measured by using a spectrophotometer and an integrating sphere unit as described above for the measurement of scattering transmittance/straight transmittance of circularly polarized light, and at the time of the measurement, the measurement may be performed without using the filter which functions as the circularly polarized light filter on the light source side.

The circularly polarized light separation layer may be formed of only a reflected light non-scattering circularly polarized light separation layer which does not have reflected light scattering properties described above, may be formed of only the reflected light scattering circularly polarized light separation layer, or may be formed of the reflected light scattering circularly polarized light separation layer and the reflected light non-scattering circularly polarized light separation layer. In a case of a circularly polarized light separation layer formed of the reflected light scattering circularly polarized light separation layer and the reflected light non-scattering circularly polarized light separation layer, it is preferable that the reflected light scattering circularly polarized light separation layer is included on the outermost surface.

Regarding the reflected light non-scattering circularly polarized light separation layer, the scattering properties of reflected light and transmitted light with respect to the circularly polarized light at a specific wavelength (selective reflection wavelength) of one sense are substantially the same as the scattering properties with respect to the circularly polarized light having the opposite sense, a value of scattering transmittance/straight transmittance of circularly polarized light having the sense at the specific wavelength is 0.00 to 0.05 and preferably 0.00 to 0.03, and a value of diffuse reflectance/specular reflectance of circularly polarized light having the other sense is 0.0 to 0.05 and may be preferably 0.0 to 0.03. A haze value measured with natural light at the specific wavelength is equal to or smaller than 3.0 and may be preferably equal to or smaller than 1.0.

As the reflected light scattering circularly polarized light separation layer, a layer obtained by fixing a cholesteric liquid-crystalline phase may be used. As the reflected light non-scattering circularly polarized light separation layer, a layer obtained by fixing a cholesteric liquid-crystalline phase or a laminate including a linearly polarized light separation layer and a λ/4 phase difference layer may be used.

(Layer Obtained by Fixing Cholesteric Liquid-Crystalline Phase)

It is known that a cholesteric liquid-crystalline phase exhibits circularly polarized light selective reflection of selectively reflecting circularly polarized light having any one sense of right circularly polarized light and left circularly polarized light and transmitting circularly polarized light having the other sense. A number of cholesteric liquid-crystalline compounds or films formed from a cholesteric liquid-crystalline compound showing circularly polarized light selective reflection are known in the related art, and when using a layer obtained by fixing the cholesteric liquid-crystalline phase in the circularly polarized light separation film, the technologies of the related art can be referred to.

The layer obtained by fixing the cholesteric liquid-crystalline phase may be a layer in which orientation of liquid crystal compounds to be the cholesteric liquid-crystalline phases is maintained, and typically, a layer obtained by setting a polymerizable liquid crystal compound to have an orientation state of a cholesteric liquid-crystalline phase, polymerizing and curing the compound by ultraviolet light irradiation and heating to form a layer having no fluidity, and at the same time, changing the state of the compound to a state where the orientation state is not changed by an external field or an external force. In addition, in the layer obtained by fixing the cholesteric liquid-crystalline phase, it is sufficient as long as optical properties of the cholesteric liquid-crystalline phase are maintained in the layer, and the liquid crystal compound in the layer may not show liquid crystalline properties. For example, the polymerizable liquid crystal compound may be polymerized by a curing reaction and lose liquid crystalline properties.

In this specification, the layer obtained by fixing the cholesteric liquid-crystalline phase may be referred to as a cholesteric liquid-crystalline layer or a liquid crystal layer.

The cholesteric liquid-crystalline layer exhibits circularly polarized light reflection derived from a helical structure of the cholesteric liquid crystal. A center wavelength $\lambda$ of this reflection is present at intervals of a pitch length P (=period of helix) of the helical structure of the cholesteric phase, and satisfies a relationship of $\lambda = n \times P$ with respect to the average refractive index n of the cholesteric liquid-crystalline layer. Accordingly, it is possible to adjust the wavelength showing the circularly polarized light reflection by adjusting the pitch length of the helical structure. That is, the n value and the P value may be adjusted to set the center wavelength $\lambda$ in a wavelength range of 380 nm to 780 nm, so as to allow selective transmission (reflection) of light in at least a part of the visible light wavelength range. In addition, the center wavelength $\lambda$ may be set to be in a wavelength range of 780 nm to 1500 nm and preferably in a wavelength range of 800 nm to 1500 nm by adjusting the n value and the P value described above, so that any one of right circularly polarized light and left circularly polarized light is selectively transmitted (reflected) in at least a part of the near infrared light wavelength range.

Figure 1B:
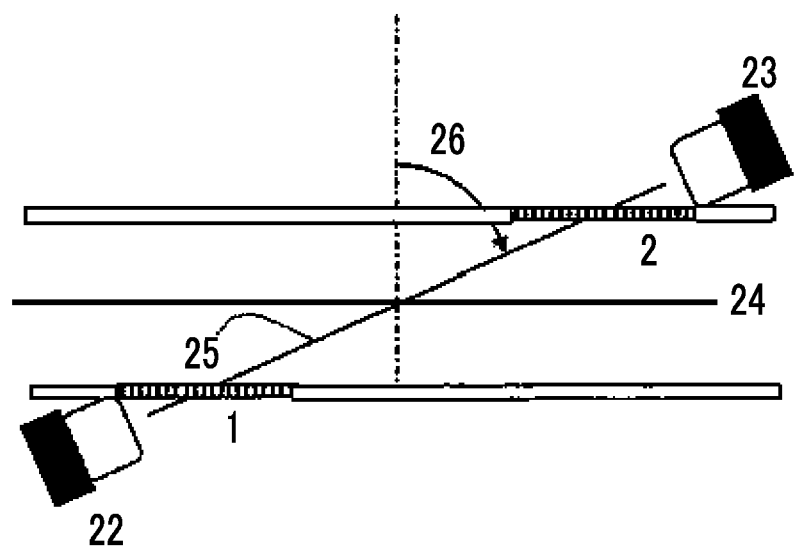
Figure 1C:
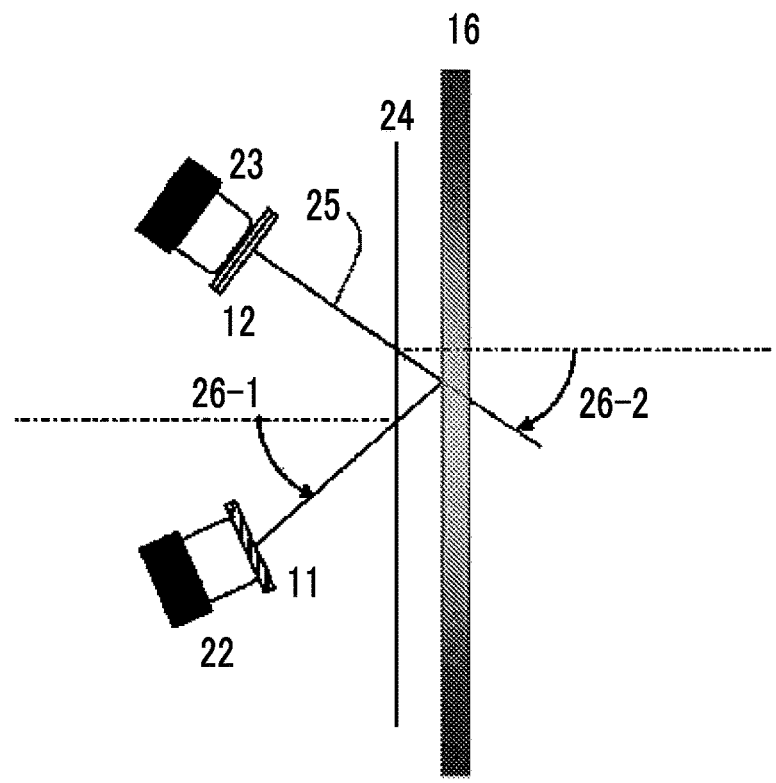
Figure 1D:
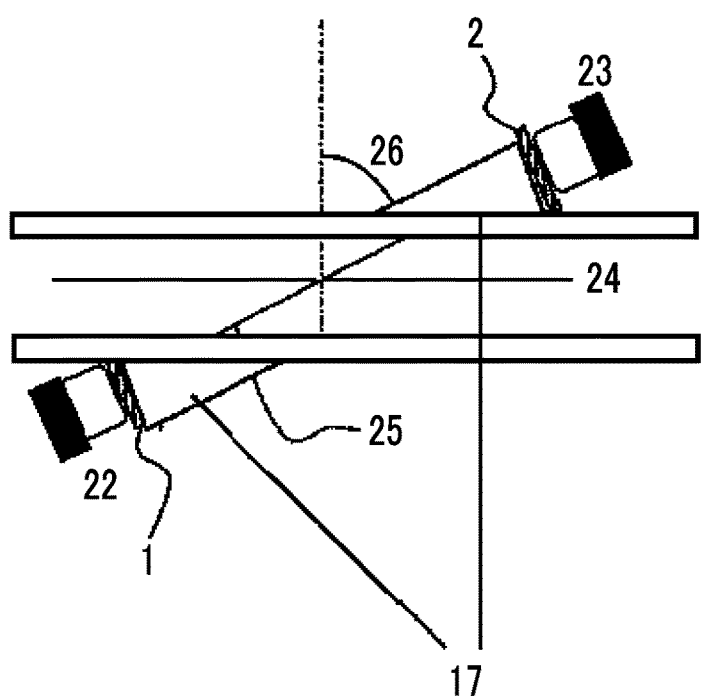

In a case where light is obliquely incident to the cholesteric liquid-crystalline layer, as in a case of using the cholesteric liquid-crystalline layer in the circularly polarized light separation film 1 or the circularly polarized light separation film 2 in the arrangement B of FIG. 1B, for example, the center wavelength of the selective reflection is shifted to the short wavelength side. Accordingly, it is preferable to adjust the value of n×P so that $\lambda$ calculated based on the expression of $\lambda = n \times P$ described above becomes a longer wavelength than a wavelength of the selective reflection necessary in accordance with the light source or the light receiving element. In a case where the center wavelength in the selective reflection in a case where a light ray passes through a cholesteric liquid-crystalline layer having a refractive index $n_2$ by an angle of $\theta_2$ with respect to the normal direction of the cholesteric liquid-crystalline layer (screw axis direction of cholesteric liquid-crystalline layer) is set as $\lambda_d$, a value of $\lambda_d$ is represented with the following expression.

$$\lambda_d = n_2 \times P \times \cos \theta_2$$

A value of $\theta_2$ when light is incident to the cholesteric liquid-crystalline layer having a refractive index $n_2$ from the air space having a refractive index of 1.0 by an angle of $\theta_1$ with respect to the normal direction of the cholesteric liquid-crystalline layer is represented with the following expression.

$$\theta_2 = \arcsin(\sin \theta_1 / n_2)$$

In a case where light is obliquely incident to the cholesteric liquid-crystalline layer, a desired center wavelength may be set by adjusting the n value and the P value based on the expression described above.

Since the pitch length of the cholesteric liquid-crystalline phase is dependent on the types of a chiral agent used with the polymerizable liquid crystal compound or added concentration thereof, a desirable pitch length can be obtained by adjusting these. As a measuring method of the sense or pitch of the helix, methods disclosed in "Introduction: Liquid Crystal Experiments" (edited by the Japanese Liquid Crystal Society, Sigma Publications, published in 2007 p. 46) and "Liquid Crystal Handbook" (Liquid Crystal Handbook Editorial Committee, Maruzen Publishing, p. 196) can be used.

In addition, regarding the half-wavelength of the selective reflection (circularly polarized light reflection) range, $\Delta\lambda$ is dependent on a birefringence $\Delta n$ of the liquid crystal compound and the pitch length P and satisfies a relationship of $\Delta\lambda = \Delta n \times P$. Accordingly, the width of the selective reflection range can be controlled by adjusting $\Delta n$. The adjustment of $\Delta n$ can be performed by adjusting the types of polymerizable liquid crystal compound or a mixing ratio thereof, or controlling a temperature at the time of orientation fixation.

Since the width of the circularly polarized light reflection wavelength range in the visible light region is 50 nm to 150 nm with a material in general, it is possible to enlarge the bandwidth of the reflection by laminating several types of cholesteric liquid-crystalline layers having different center wavelengths of the reflected light due to changes in the period P. In addition, in one cholesteric liquid-crystalline layer, it is possible to enlarge the bandwidth of the reflection by gradually changing the period P with respect to a film thickness direction.

In addition, the sense of the reflected circularly polarized light of the cholesteric liquid-crystalline layer coincides with the sense of the helix.

As the circularly polarized light separation layer, a cholesteric liquid-crystalline layer having the sense of helix is right or left may be used, or when lamination is performed in order to increase circularly polarized light selectivity at a specific wavelength, a plurality of cholesteric liquid-crystalline layers having the same period P and the same sense of helix may be laminated. At that time, a cholesteric liquid-crystalline layer separately prepared by using a method which will be described later may be bonded with an adhesive layer or the like, or a liquid crystal composition including a polymerizable liquid crystal compound may be directly applied to the surface of a preexisting cholesteric liquid-crystalline layer which is formed by a method which will be described later, and laminated by repeating steps of orientation and fixation. By performing the latter method, an orientation alignment of liquid crystal molecules on an air interface side of the cholesteric liquid-crystalline layer previously formed, and an orientation alignment of liquid crystal molecules on the lower side of the cholesteric liquid-crystalline layer formed thereon coincide with each other, and the light polarization properties of the circularly polarized light separation layer are improved.

In addition, a plurality of layers may be laminated in order to enlarge the selective reflection (transmission) wavelength bandwidth, and at that time, the cholesteric liquid-crystalline layer having the same sense of helix may be laminated.

The cholesteric liquid-crystalline layer can selectively allow the transmission of any one of right circularly polarized light and left circularly polarized light even with respect to light incident from any surface, and can separate even light incident from any surface into right circularly polarized light and left circularly polarized light and selectively allow the transmission of any one thereof to the other side surface.

Hereinafter, manufacturing materials and a manufacturing method of the cholesteric liquid-crystalline layer which can be used in the visible light reflection layer or the circularly polarized light separation layer will be described.

As the materials used for the formation of the cholesteric liquid-crystalline layer, a liquid crystal composition containing the polymerizable liquid crystal compound and the chiral agent (optically active compound) are used. If necessary, a liquid crystal composition obtained by additionally mixing in a surfactant or a polymerization initiator and dissolving the mixture in a solution is applied to the base material (a support, an oriented layer, a transparent layer, or the cholesteric liquid-crystalline layer as a lower layer), cholesteric orientation and aging is performed, and fixed to form the cholesteric liquid-crystalline layer.

Polymerizable Liquid Crystal Compound

The polymerizable liquid crystal compound may be a rod-like liquid crystal compound or a disk-like liquid crystal compound, and a rod-like liquid crystal compound is preferably used.

As an example of a rod-like polymerizable liquid crystal compound for forming the cholesteric liquid-crystalline layer, a rod-like nematic liquid crystal compound may be used. As a rod-like nematic liquid crystal compound, azomethines, azoxys, cyano biphenyls, cyanophenyl esters, benzoic acid esters, cyclohexane carboxylic acid phenyl esters, cyanophenyl cyclohexanes, cyano-substituted phenyl pyrimidines, alkoxy-substituted phenyl pyrimidines, phenyl dioxanes, tolanes, and alkenylcyclohexylbenzonitriles are preferably used. Not only a low-molecular-weight liquid crystal compound, but also a high-molecular-weight liquid crystal compound can be used.

A polymerizable cholesteric liquid-crystalline compound is obtained by introducing a polymerizable group to the cholesteric liquid-crystalline compound. Examples of the polymerizable group include an unsaturated coincidence group, an epoxy group, and an aziridinyl group, an unsaturated polymerizable group is preferable and an ethylenically unsaturated polymerizable group is particularly preferable. The polymerizable group can be introduced into molecules of the cholesteric liquid-crystalline compound by various methods. The number of polymerizable groups included by the polymerizable cholesteric liquid-crystalline compound is preferably 1 to 6 and more preferably 1 to 3. Examples of the polymerizable cholesteric liquid-crystalline compound include compounds disclosed in Makromol. Chem., vol. 190, 2255 p, (1989), Advanced Materials, vol. 5, 107 p (1993), U.S. Pat. No. 4,683,327A, U.S. Pat. No. 5,622, 648A, U.S. Pat. No. 5,770,107A, WO95/22586A, WO95/24455A, WO97/00600A, WO98/23580A, WO98/52905A, JP1989-272551A (JP-H01-272551A), JP1994-16616A (JP-H06-16616A), JP1995-110469A (JP-H07-110469A), JP1999-80081A (JP-H11-80081), and JP2001-328973A. Two or more types of polymerizable cholesteric liquid-crystalline compound may be used in combination. In a case where two or more types of polymerizable cholesteric liquid-crystalline compound are used in combination, it is possible to decrease the orientation temperature.

In addition, the added amount of the polymerizable liquid crystal compound in the liquid crystal composition is preferably 80 to 99.9% by mass, more preferably 85 to 99.5% by mass, and particularly preferably 90 to 99% by mass, with respect to the solid content mass (mass excluding the solvent) of the liquid crystal composition.

Chiral Agent (Optically Active Compound)

The chiral agent has a function of causing the helical structure of the cholesteric liquid-crystalline phase. Since the sense of helix or the helical pitch varies according to the compound, the chiral compound may be selected according to the purpose.

The chiral agent is not particularly limited, and well-known compounds (for example, Liquid Crystal Device Handbook, third vol. paragraphs 4-3, a chiral agent for TN or STN, p. 199, Japan Society for the Promotion of Science 142th Committee Edition, 1989), isosorbide, or an isomannide derivative can be used.

The chiral agent generally includes asymmetric carbon atoms, but an axial asymmetric compound or a planar asymmetric compound not including asymmetric carbon atoms can be used as the chiral agent. As an example of an axial asymmetric compound or a planar asymmetric compound, binaphthyl, helicene, paracyclophane, and derivatives thereof are included. The chiral agent may include a polymerizable group. In a case where the chiral agent and a curable cholesteric liquid-crystalline compound include a polymerizable group, it is possible to form a polymer including a repeating unit derived from the cholesteric liquid-crystalline compound and a repeating unit derived from the chiral agent, by the polymerization reaction between the polymerizable chiral agent and the polymerizable cholesteric liquid-crystalline compound. In this aspect, the polymerizable group included in the polymerizable chiral agent is preferably the same type of group as the polymerizable group included in the polymerizable cholesteric liquid-crystalline compound. Accordingly, the polymerizable group of the chiral agent is preferably an unsaturated polymerizable group, an epoxy group, or an aziridinyl group, more preferably an unsaturated polymerizable group, and particularly preferably an ethylenically unsaturated polymerizable group.

In addition, the chiral agent may be a liquid crystal compound.

It is preferable that the chiral agent includes a photoisomerization group, because a pattern having a desired reflection wavelength corresponding to an emission wavelength can be formed by photomask exposure of active light after coating and orientation. As the photoisomerization group, an isomerization part of a compound showing photochromic properties, azo, azoxy, and cinnamoyl groups are preferable. As specific compounds, compounds disclosed in JP2002-80478A, JP2002-80851A, JP2002-179668A, JP2002-179669A, JP2002-179670A, JP2002-179681A, JP2002-179682A, JP2002-338575A, JP2002-338668A, JP2003-313189A, and JP2003-313292A can be used.

The content of the chiral agent in the liquid crystal composition is preferably 0.01% mol to 200% mol and more preferably 1% mol to 30% mol of the amount of the polymerizable liquid crystal compound.

Polymerization Initiator

The liquid crystal composition preferably contains a polymerization initiator. In a case of causing the polymerization reaction to proceed using the ultraviolet light irradiation, the polymerization initiator used is preferably a photopolymerization initiator which can start the polymerization reaction by an ultraviolet light irradiation. Examples of the photopolymerization initiator include an α-carbonyl compound (disclosed in each specification of U.S. Pat. Nos. 2,367,661A and 2,367,670A), acyloin ether (disclosed in the specification of U.S. Pat. No. 2,448,828A), a α-hydrocarbon-substituted aromatic acyloin compound (disclosed in the specification of U.S. Pat. No. 2,722,512A), a polynuclear quinone compound (disclosed in each specification of U.S. Pat. Nos. 3,046,127A and 2,951,758), a combination of a triaryl imidazole dimer and p-amino phenyl ketone (disclosed in the specification of U.S. Pat. No. 3,549,367A), acridine and phenazine compounds (disclosed in each specification of JP1985-105667A (JP-S60-105667A) and U.S.

Pat. No. 4,239,850A), and an oxadiazole compound (disclosed in the specification of U.S. Pat. No. 4,212,970A).

The content of the photopolymerization initiator in the liquid crystal composition is preferably 0.1% by mass to 20% by mass and more preferably 0.5% by mass to 5% by mass, with respect to the content of the polymerizable liquid crystal compound.

Cross-Linking Agent

The liquid crystal composition may contain an arbitrary cross-linking agent, in order to improve film strength after the curing and durability. As the cross-linking agent, a material which is cured by ultraviolet light, heat, or humidity can be preferably used.

The cross-linking agent is not particularly limited and can be suitably selected according to the purpose, and examples thereof include a multifunctional acrylate compound such as trimethylolpropane tri(meth)acrylate or pentaerythritol tri (meth)acrylate; an epoxy compound such as glycidyl (meth) acrylate or ethylene glycol diglycidyl ether; an aziridine compound such as 2,2-bishydroxymethylbutanol-tris[3-(1-aziridinyl)propionate] or 4,4-bis (ethylene iminocarbonyl amino)diphenylmethane; an isocyanate compound such as hexamethylene diisocyanate or biuret type isocyanate; a polyoxazoline compound including an oxazoline group as a side chain; and an alkoxysilane compound such as vinyltrimethoxysilane or N-(2-aminoethyl)-3-aminopropyltrimethoxysilane. In addition, a well-known catalyst can be used according to the reactivity of the cross-linking agent and it is possible to improve productivity, in addition to the film strength and durability. These may be used alone or in combination of two or more kinds thereof.

The content of the cross-linking agent is preferably 3% by mass to 20% by mass and more preferably 5% by mass to 15% by mass. In a case where the content of the cross-linking agent is smaller than 3% by mass, an effect of the improvement in crosslinking density may not be obtained, and in a case where the content thereof exceeds 20% by mass, stability of the cholesteric layer may be lower.

Orientation Controlling Agent

An orientation controlling agent which contributes to stable and rapid formation of a planar orientation in a cholesteric liquid-crystalline layer may be added to the liquid crystal composition. Examples of the orientation controlling agent include a fluorine (meth)acrylate polymer disclosed in Paragraphs [0018] to [0043] of JP2007-272185A and compounds represented by Formulae (I) to (IV) disclosed in Paragraphs [0031] to [0034] of JP2012-203237A.

In addition, as the orientation controlling agent, these may be used alone or in combination of two or more kinds thereof.

The added amount of the orientation controlling agent in the liquid crystal composition is preferably 0.01% by mass to 10% by mass, more preferably 0.01% by mass to 5% by mass, and particularly preferably 0.02% by mass to 1% by mass, with respect to the entire mass of the cholesteric liquid-crystalline compound.

Other Additives

Other liquid crystal compositions may contain at least one kind selected from various additives such as a surfactant for adjusting surface tension of a coated film to obtain an even film thickness, and a polymerizable monomer. Further, if necessary, a polymerization inhibitor, an antioxidant, an ultraviolet absorbing agent, a light stabilizer, a coloring material, and metal oxide fine particles can be added to the liquid crystal composition, in a range not decreasing the optical properties.

A cholesteric liquid-crystalline layer in which cholesteric regularity is fixed can be formed, by applying a liquid crystal composition obtained by dissolving the polymerizable liquid crystal compound and the polymerization initiator, and if necessary, the chiral agent and the surfactant in a solvent, on the base material, obtaining a dried coated film, and irradiating this coated film with active light to polymerize the cholesteric liquid-crystalline composition. In addition, a laminated film formed of a plurality of cholesteric layers can be formed by repeating the manufacturing step of the cholesteric layer.

The solvent used in the preparation of the liquid crystal composition is not particularly limited and can be suitably selected according to the purpose, and an organic solvent is preferably used.

The organic solvent is not particularly limited and can be suitably selected according to the purpose, and examples thereof include ketones, alkyl halides, amides, sulfoxides, heterocyclic compounds, hydrocarbons, esters, and ethers. These may be used alone or in combination of two or more kinds thereof. Among these, ketones are particularly preferable, when environmental load is considered.

A method of applying the liquid crystal composition to the base material is not particularly limited and can be suitably selected according to the purpose, and examples thereof include a wire bar coating method, a curtain coating method, an extrusion coating method, a direct gravure coating method, a reverse gravure coating method, a die-coating method, a spin coating method, a dip coating method, a spray coating method, and a slide coating method. In addition, the application can be executed by transferring the liquid crystal composition applied to an additional support to the base material. The liquid crystal molecules are oriented by heating the applied liquid crystal composition. The heating temperature is preferably equal to or lower than 200° C. and more preferably equal to or lower than 130° C. By performing this orientation process, an optical thin film in which the polymerizable liquid crystal compound is twist-oriented so as to have a screw axis substantially orthogonal to a film surface is obtained.

The oriented liquid crystal compound may be further polymerized. The polymerization may be any of thermal polymerization and photopolymerization performed by light irradiation, and photopolymerization is preferable. The light irradiation is preferably performed using ultraviolet light. The irradiation energy is preferably 20 mJ/cm$^2$ to 50 J/cm$^2$ and more preferably 100 mJ/cm$^2$ to 1500 mJ/cm$^2$. In order to promote the photopolymerization reaction, the light irradiation may be executed under heating conditions or a nitrogen atmosphere. The emitted ultraviolet light wavelength is preferably 350 nm to 430 nm. The polymerization reaction rate is preferably high, preferably equal to or greater than 70%, and more preferably equal to or greater than 80%, from a viewpoint of stability.

The polymerization reaction rate can be determined by measuring the rate of consumption of the polymerizable functional group using an IR absorption spectrum.

In addition, the thickness (total of the plurality of layers, when the plurality of layers are laminated) of the cholesteric liquid-crystalline layer which is the circularly polarized light separation layer is preferably 1 μm to 150 μm, more preferably 1 μm to 100 μm, even more preferably 1.5 μm to 30 μm, and particularly preferably 2 μm to 15 μm.

(Adjustment of Diffuse Reflectance/Specular Reflectance of Cholesteric Liquid-Crystalline Layer)

As a result of the research of the inventors, it is clear that a liquid crystal layer having high diffuse reflectance at a specific wavelength has a small tilt angle of liquid crystal molecules at least on one surface of the layer, preferably both surfaces of the layer and is obtained by setting in-plane orientation azimuth of liquid crystal molecules random. That is, it is possible to adjust the diffuse reflectance at a selective reflection wavelength by adjusting the tilt angle and the in-plane orientation azimuth described above. The liquid crystal orientation azimuth and the tilt angle in the vicinity of the surface of the cholesteric liquid-crystalline layer may be confirmed by observing the vicinity of the film surface of the cross section of the cholesteric liquid-crystalline layer with a transmission electron microscope (TEM) image.

By adjusting the tilt angle and the in-plane orientation azimuth of liquid crystal molecules of the surface of the cholesteric liquid-crystalline layer as described above, it is possible to realize a configuration including an inclination of a screw axis of the cholesteric liquid-crystalline phase on the outermost surface. The expression "including an inclination of a screw axis" means that inclination of the screw axis which will be described later is equal to or greater than 2° in the plane. It is considered that the screw axis of the cholesteric liquid-crystalline phase is distributed with slight undulation in the plane by using the configuration including an inclination of a screw axis of the cholesteric liquid-crystalline phase on the outermost surface. That is, the deviation of the screw axis from the normal direction of the layer can be generated. A scattering layer having high diffuse reflectance/specular reflectance is obtained due to the deviation of the screw axis. A plurality of orientation defects may be generated in this layer.

The inclination of the screw axis on the outermost surface of the cholesteric liquid-crystalline layer can be obtained as follows.

When the cross section of the cholesteric liquid-crystalline layer is observed with TEM, a stripe pattern of bright parts and dark parts can be observed. The stripe pattern is observed so that bright parts and dark parts are repeated in a direction substantially parallel with the layer surface. The repeating of these bright parts and dark parts two times (two bright parts and two dark parts) corresponds to 1 pitch of a helix. The normal direction of the stripe pattern is a screw axis. The inclination of the screw axis on the outermost surface of the cholesteric liquid-crystalline layer can be obtained as an angle formed with a line formed by the first dark part from the outermost surface and the outermost surface on the same side.

By setting the cholesteric liquid-crystalline layer to have a configuration so that the inclination of the screw axis on the outermost surface changes in the plane, it is possible to obtain a reflected light scattering circularly polarized light separation layer having high diffuse reflectance/specular reflectance. The expression "the inclination of the screw axis changes", for example, shows a state in which, when the inclination of the screw axis is measured on an arbitrary straight line of the surface at regular intervals, an increase and a decrease of the inclination are confirmed in a linear progressing direction. The increase and decrease are preferably repeated and it is preferable that the change consecutively occurs.

The outermost surface may be at least any one surfaces (uppermost surface or the lowermost surface) of the cholesteric liquid-crystalline layer or may be both surfaces (uppermost surface or the lowermost surface), and is preferably both surfaces.

A maximum value of the inclination of the screw axis may be approximately equal to or smaller than 20°. The maximum value of the inclination of the screw axis may be 2° C. to 20° and is preferably 5° to 20°.

In this specification, the term "tilt angle" means an angle formed with inclined liquid crystal molecules and a layer plane, and means a maximum angle among angles formed with a direction of a refractive index ellipsoid of a liquid crystal compound having the maximum refractive index and the layer plane. Accordingly, in the rod-like liquid crystal compound having positive optical anisotropy, the tilt angle means an angle formed with a long axis direction of the rod-like liquid crystal compound, that is, a director direction and the layer plane.

The in-plane orientation azimuth of liquid crystal molecules means an azimuth in the plane parallel to the layer in a direction of the liquid crystal molecules having the maximum refractive index. The expression "the in-plane orientation azimuth is random" means a state in which 10% to 20% of the liquid crystal molecules having the in-plane orientation azimuth which is different from the average azimuth of the in-plane orientation azimuths of liquid crystal molecules in the plane by 4° or more can be confirmed by using a TEM.

In this specification, the term "liquid crystal molecules" means molecules of a polymerizable liquid crystal compound in a liquid crystal composition, and means a partial structure corresponding to the polymerizable liquid crystal compound, in a case where the polymerizable liquid crystal compound is polymerized due to a curing reaction of the liquid crystal composition.

A tilt angle of liquid crystal molecules on the surface on the lower layer side when arranging the polymerizable liquid crystal compound when forming the cholesteric liquid-crystalline layer is preferably in a range of 0° to 20° and more preferably 0° to 10°. By controlling the tilt angle to be the values described above, it is possible to set a density of orientation defects and tilt angle distribution of the screw axis to be in preferable ranges.

At the time of the orientation of the polymerizable liquid crystal compound when forming the cholesteric liquid-crystalline layer for forming the reflected light scattering circularly polarized light separation layer, a tilt angle (pretilt angle) of the liquid crystal molecules on the surface on the lower layer side is set to be small as described above or is preferably horizontal (parallel to a surface of a support). In addition, in order to decrease orientation uniformity of the liquid crystal molecules, it is preferable not to perform orientation treatment such as rubbing on the surface of a transparent layer, a base material, or other cholesteric liquid-crystalline layer which will be described later to be coated with the liquid crystal composition. It is preferable to use the orientation controlling agent in order to set the tilt angle the liquid crystal molecules on an air interface side of the cholesteric liquid-crystalline layer to be horizontal.

(Laminate Including Linearly Polarized Light Separation Layer and λ/4 Phase Difference Layer)

In the circularly polarized light separation layer formed of the laminate including the linearly polarized light separation layer and the λ/4 phase difference layer, light emitted from the surface of the linearly polarized light separation layer is converted into linearly polarized light by reflection or absorption and then converted into right or left circularly polarized light by passing through the λ/4 phase difference layer. Meanwhile, in a case of light emission from the λ/4 phase difference layer, light in any polarized state becomes linearly polarized light by finally passing through the linearly polarized light separation layer, but specifically, in a case where the incidence ray is circularly polarized light, the light is converted into the linearly polarized light which is parallel to or orthogonal to a transmission axis of the linearly polarized light layer by the λ/4 phase difference layer, and accordingly, in order to use the light in recognition of the sense of the incident circularly polarized light, the light is preferably emitted from the λ/4 phase difference layer side, and when using the emitting circularly polarized light, the light is preferably emitted from the linearly polarized light separation layer side.

As the linearly polarized light separation layer, a linear polarizer can be used or a polarizer corresponding to the wavelength range of light used may be used.

Linear Polarizer

As the infrared linear polarizer which can be preferably used, a multilayer dielectric reflection polarizer in which a plurality of layers of resins having refractivity and different refractive indexes from each other are laminated and a thickness and a phase difference value are controlled by stretching, a grid polarizer configured with a number of parallel conductor line arrangements (grid), a polarizer in which metal nanoparticles having shape anisotropy are arranged and fixed, or a polarizer in which dichroic pigments are arranged and fixed, is used. All of these are easily formed in a thin layer shape, a film shape, or a plate shape, and can be formed by simply bonding a sheet-like phase difference layer which will be described later, in a step of forming the circularly polarized light separation layer. Alternatively, the phase difference layer can be formed by directly applying a composition for phase difference layer formation onto the infrared linear polarizer, and thus a thinner circularly polarized light separation layer can be manufactured.

The multilayer dielectric reflection polarizer is a polarizing film which transmits only the light in a vibration direction parallel to the plane transmission axis and reflects the other light. As such a film, a multilayer film disclosed in JP1997-507308A (JP-H09-507308A) can be used. This is obtained by alternatively laminating a layer formed of the transparent dielectric layer 1 not having birefringence in the film surface and a layer formed of the transparent dielectric layer 2 having birefringence in a surface, and is formed so that a refractive index of the transparent dielectric layer 1 coincides with any one of an ordinary light refractive index and an extraordinary light refractive index of the transparent dielectric layer 2. In addition, at least any one of the transparent dielectric layers is configured so that the product (n×d) of the thickness (d) and the refractive index (n) of the transparent dielectric layer becomes ¼ of the wavelength of the light to be reflected. The material for forming the transparent dielectric layers may be materials having light-transmitting properties at the infrared light wavelength used, and examples thereof include polycarbonate, an acrylic resin, polyester, an epoxy resin, polyurethane, polyamide, polyolefin, a cellulose derivative, or silicone (including modified silicone such as silicone polyurea).

The grid polarizer is obtained by providing a plurality of parallel conductor line arrangement structures (grids) having a submicron pitch (pitch shorter than the wavelength of the incidence ray) formed of a good conductor thin film such as aluminum, silver, or gold, on one surface of a polymer film having light-transmitting properties at the infrared light wavelength used, a glass substrate or a silicon (Si) substrate, and a polarizer disclosed in JP2002-328234A can be used. This polarizer functions as a polarizer by reflecting the polarized light component parallel to a grid in the incidence ray and transmitting the polarized light component orthogonal thereto. If necessary, this can be interposed between the glass or an anti-reflection layer can be provided.

The polarizer in which metal nanoparticles having shape anisotropy are oriented and fixed is obtained by orienting and fixing silver halide particles or silver particles having a great aspect ratio. This polarizer is an absorption type linear polarizing plate which absorbs infrared light having an electric field vibration surface in the arrangement direction of the particles and transmits the infrared light in a direction orthogonal thereto. As an example thereof, polarizing plates disclosed in JP1984-83951A (JP-S59-83951A), JP1990-248341A (JP-H02-248341A), and JP2003-139951A can be used.

As the polarizer in which dichroic pigments are arranged and fixed, an infrared polarizing film in which iodine is adsorbed or dichroic dye is doped in PVA (polyvinyl alcohol) and stretched to make polyvinylene can be used. This polarizer absorbs the infrared light having an electric field vibration surface in the stretching direction and transmits the infrared light in the direction orthogonal thereto.

This can obtain the orientation of dichroic pigments by performing dyeing of a PVA layer by passing through the PVA film in a dye composition tank of iodine/iodide and stretching the layer by a factor of 4 to 6 times. The conversion of PVA to polyvinylene can be performed by a hydrochloric acid vapor method disclosed in U.S. Pat. No. 2,445,555A. In addition, in order to improve stability of the materials for polarization, boration of the material into is also performed by using an aqueous borate bath containing boric acid and borax. A commercially available linearly polarized light film manufactured by Edmund Optics Japan can be used as a product corresponding thereto.

The thickness of the linearly polarized light separation layer is preferably 0.05 μm to 300 μm, more preferably 0.2 μm to 150 μm, and even more preferably 0.5 μm to 100 μm.

λ/4 Phase Difference Layer

An in-plane slow axis of a phase difference plate is present at an alignment rotated by 45° from the absorption axis or the transmission axis of the polarizing plate. In a case where a single light source such as an LED or a laser is used as the infrared light source, the front surface phase difference of the phase difference plate is desirably a length of ¼ of the center wavelength of the emission wavelength of the light source or "center wavelength * n±¼ of center wavelength (n is an integer)", and for example, when the emission center wavelength of the light source is 1000 nm, the phase difference of 250 nm, 750 nm, 1250 nm, or 1750 nm is preferable. In addition, small dependency of the phase difference on the light incidence angle is preferable, and a phase difference plate having a phase difference of a length of ¼ of the center wavelength is most preferable from this viewpoint.

In the sensing system or the sensing method of the invention, when various types of light source having different emission wavelengths are used in combination as the infrared light source, or a light source in which there is a peak in the light emission intensity at greater than or equal to two wavelengths or a light source in which the light emission is performed in a wide wavelength range is used, a case of enlarging the wavelength range showing the circularly polarized light selectivity is considered. Even in such a case, the phase difference plate described above can be used, but it is more preferable to use a phase difference plate having a wide range. A phase difference plate having a wide range is a phase difference plate in which a phase difference angle is constant over the wide wavelength range. Examples thereof include a laminated phase difference plate in which phase difference layers having different wavelength dispersions of the birefringence from each other are set to be orthogonal to the slow axis thereof to have a wide range, a polymer film in which substituents having different wavelength dispersions of the birefringence from each other are set to be orthogonal to an arrangement axis thereof using the principle described above at a molecular level to perform the orientation formation, or a phase difference plate in which a layer of λ/2 which is the phase difference with respect to the wavelength (λ) in the wavelength range used and a layer of λ/4 are laminated by being caused to intersect the slow axis thereof at 60°.

Examples of the material of the phase difference plate include crystalline glass or crystal of an inorganic material, a polymer such as polycarbonate, an acrylic resin, polyester, an epoxy resin, polyurethane, polyamide, polyolefin, a cellulose derivative, or silicone (including modified silicone such as silicone polyurea), or a material in which polymerizable liquid crystal compounds or polymer liquid crystal compounds are arranged and fixed.

The thickness of the λ/4 layer is preferably 0.2 μm to 300 μm, more preferably 0.5 μm to 150 μm, and even more preferably 1 μm to 80 μm.

(Other Layers)

The circularly polarized light separation film may include other layers such as a support, an orientation layer for causing the orientation of the liquid crystal compound, an adhesion layer for adhering the circularly polarized light separation layer and the visible light shielding layer to each other, and a light shielding layer for not allowing the transmission of light at a wavelength beyond the specific wavelength range used in the sensing.

(Support)

The support is not particularly limited and a plastic film or glass may be used as an example. It is preferable that the support does not have a property of offsetting the optical properties of the visible light shielding layer or the circularly polarized light separation layer, and the support is generally transparent and preferably has low birefringence. Examples of the plastic film include polyester such as polyethylene terephthalate (PET), polycarbonate, an acrylic resin, an epoxy resin, polyurethane, polyamide, polyolefin, a cellulose derivative, and silicone. The support used for manufacturing the cholesteric liquid-crystalline layer may be peeled off from the circularly polarized light separation film.

In a case of using a circularly polarized light separation film including a support and a circularly polarized light separation layer in the emission unit, it is preferable that the support side of the circularly polarized light separation layer becomes the light source side. In addition, in a case of using a circularly polarized light separation film including a support and a circularly polarized light separation layer in the detection unit, the support side of the circularly polarized light separation layer becomes the light receiving element side.

(Orientation Layer)

The orientation film can be provided by means of rubbing treatment of an organic compound and a polymer (a resin such as polyimide, polyvinyl alcohol, polyester, polyarylate, polyamideimide, polyetherimide, polyamide, or modified polyamide), oblique vapor deposition of an inorganic compound, formation of a layer having a microgroove, or accumulation of an organic compound (for example, ω-tricosanoic acid, dioctadecyl methyl ammonium chloride, or methyl stearate) by a Langmuir-Blodgett method (LB film). In addition, an orientation layer which has an orientation function by applying an electric field, applying a magnetic field, or performing light irradiation is also known. Among these, the orientation film formed by the rubbing treatment of the polymer is particularly preferable. The rubbing treatment can be executed by rubbing the surface of the polymer layer several times in a given direction with paper or a fabric.

The liquid crystal composition may be applied to the surface of the support or the surface on which the rubbing treatment of the support is performed, without providing the orientation layer.

(Transparent Layer)

At the time of preparing the reflected light scattering circularly polarized light separation layer, a transparent layer may be included as a lower layer coated with a liquid crystal composition when forming the cholesteric liquid-crystalline layer. As the transparent layer, a layer formed of a material which applies a low pretilt angle to the polymerizable liquid crystal compound molecules in the liquid crystal composition provided on the surface thereof can be preferably used.

As the transparent layer, a layer obtained by applying and curing a non-liquid crystal polymerizable composition including (meth)acrylate monomers, gelatin, or urethane monomers can be used. An acrylic layer obtained by applying and curing a layer including (meth)acrylate monomers is isotropic in the plane, for example, and accordingly, when a liquid crystal layer is formed without performing rubbing treatment on the surface of the acrylic layer, the in-plane orientation azimuth of liquid crystals coming into contact with the acrylic layer becomes random.

Thus, the cholesteric liquid-crystalline layer formed by applying the liquid crystal composition to the surface of the acrylic layer can be set as a layer having orientation defects. When a liquid crystal layer is formed on the liquid crystal layer having orientation defects, a liquid crystal layer having orientation defects can be formed in the same manner.

In addition, as the transparent layer, a resin such as polyimide (SUNEVER 130 which is polyimide varnish manufactured by Nissan Chemical Industries, Ltd.), polyvinyl alcohol, polyester, polyarylate, polyamideimide, polyetherimide, polyamide, or modified polyamide may be used. It is preferable not to perform rubbing treatment (for example, rubbing treatment of rubbing a surface of a polymer layer in a certain direction by using paper or cloth) on the surface of the transparent layer coated with the liquid crystal composition, in order to form a cholesteric liquid-crystalline layer having high diffuse reflectance.

A thickness of the transparent layer is preferably 0.01 to 50 μm and more preferably 0.05 to 20 μm.

(Adhesive Layer)

An adhesive may be a hot melt type, a heat curing type, a photocuring type, a reactive curing type, and a pressure sensitive adhesion type which does not need curing from a viewpoint of the curing method, and as a material of each type, acrylate, urethane, urethane acrylate, epoxy, epoxy acrylate, polyolefin, modified olefin, polypropylene, ethylene vinyl alcohol, vinyl chloride, chloroprene rubber, cyanoacrylate, polyamide, polyimide, polystyrene, and polyvinyl butyral compounds can be used. The curing method is preferably the photocuring type, from the viewpoints of workability and productivity, and as the material, an acrylate, urethane acrylate, or epoxy acrylate compound is preferably used, from the viewpoints of optical transparency and heat resistance.

(Light Shielding Layer)

The circularly polarized light separation film preferably has low light transmittance with respect to light at a wavelength beyond the specific wavelength range. The light shielding layer is provided in order to shield light at a wavelength beyond the specific wavelength range.

As the light shielding layer, a light reflection layer or a light absorption layer is used.

As an example of the light reflection layer, a dielectric multilayer film and a cholesteric liquid-crystalline layer can be used.

The dielectric multilayer film which is a transparent dielectric is obtained by laminating a plurality of layers of inorganic oxide or an organic polymer material having different refractive indexes. A layer of the inorganic oxide can be, for example, formed on a surface of glass or a heat resistant polymer film by a sputtering method. Meanwhile, as an example of the inorganic polymer material, polycarbonate, an acrylic resin, polyester, an epoxy resin, polyurethane, polyamide, polyolefin, or silicone (including modified silicone such as silicone polyurea) is used, and the inorganic polymer material can be manufactured based on a method disclosed in JP1997-507308A (JP-H09-507308A).

The reflectance of the cholesteric liquid-crystalline layer at a reflection wavelength increases as the cholesteric liquid-crystalline layer becomes thicker, but in a general liquid crystal material, saturation is obtained with a thickness of 2 to 8 µm in the wavelength range of visible light. The reflection occurs with respect to only the circularly polarized light on one side, and accordingly, the reflectance is 50% at most. In order to perform the light reflection regardless of the sense of the circularly polarized light and to set the reflectance of natural light to be equal to or greater than 50%, as the visible light reflection layer, a laminate in which a cholesteric liquid-crystalline layer having right sense of helix and a cholesteric liquid-crystalline layer having left sense of helix having the same period P, or a laminate formed of cholesteric liquid-crystalline layers having the same period P and the same sense of helix, and a phase difference film having a phase difference of a half wavelength with respect to the center wavelength of the circularly polarized light reflection of the cholesteric liquid-crystalline layer disposed therebetween can be used.

As the light absorption layer, a layer formed by applying a dispersion obtained by dispersing a colorant such as a pigment or a dye in a solvent containing a dispersing agent and a binder or a monomer on a base material (preferably a material having a sufficient light-transmitting property in the infrared light wavelength range in which light is sensed by the light receiving element), a layer obtained by directly dying a surface of a polymer base material using a dye, or a layer formed of a polymer material containing a dye can be used.

EXAMPLES

Hereinafter, the invention will be described in more detail with reference to Examples. The materials, the reagents, the amounts of materials, the proportions thereof, the operations, and the like can be suitably modified within a range not departing from a gist of the invention. Accordingly, the range of the invention is not limited to the following Examples.

Preparation of Reflection Film MR-1 (Mirror Type)

The rubbing treatment was performed on a PET surface of COSMOSHINE A-4100 manufactured by Toyobo Co., Ltd. (thickness of 100 µm) which is not subjected easy adhesion treatment, and a coating solution A-1 shown in Table 1 was applied at room temperature so that a thickness of a dried film after drying becomes 5 µm. After drying the coating layer at room temperature for 30 seconds, the coating layer was heated in the atmosphere at 85° C. for 2 minutes, and irradiated with UV lights for 6 to 12 seconds at the output of 60% by using a D bulb (lamp, 90 mW/cm) manufactured by Fusion UV Inc. at 30° C. to prepare a liquid crystal layer. A coating solution A-2 shown in Table 1 was applied on this liquid crystal layer at room temperature so that a thickness of a dried film after drying becomes 5 µm. After drying the coating layer at room temperature for 30 seconds, the coating layer was heated in the atmosphere at 85° C. for 2 minutes, and irradiated with UV lights for 6 to 12 seconds at the output of 60% by using a D bulb (lamp, 90 mW/cm) manufactured by Fusion UV Inc. at 30° C. to prepare a liquid crystal layer. A coating solution A-3 shown in Table 1 was further applied on this liquid crystal layer at room temperature so that a thickness of a dried film after drying becomes 5 µm. After drying the coating layer at room temperature for 30 seconds, the coating layer was heated in the atmosphere at 85° C. for 2 minutes, and irradiated with UV lights for 6 to 12 seconds at the output of 60% by using a D bulb (lamp, 90 mW/cm) manufactured by Fusion UV Inc. at 30° C. to prepare a reflection film MR-1.

Preparation of Reflection Film MR-2 to MR-6 (Mirror Type)

Reflection films MR-2 to MR-6 were prepared in the same manner as in the preparation of the reflection film MR-1, except that three coating solutions shown below were respectively used, instead of the coating solutions A-1 to A-3.
  MR-2: B-1 to B-3
  MR-3: A-4 to A-6
  MR-4: B-4 to B-6
  MR-5: A-3, A-7, and A-8
  MR-6: B-3, B-7, and B-8

Preparation of Reflection Film SC-1 (Scattering Type)

The rubbing treatment was performed on a PET surface of COSMOSHINE A-4100 manufactured by Toyobo Co., Ltd. (thickness of 100 µm) which is not subjected easy adhesion treatment, and a coating solution C shown in Table 1 was applied at room temperature so that a thickness of a dried film after drying becomes 8 µm. After drying the coating layer at room temperature for 30 seconds, the coating layer was heated in the atmosphere at 85° C. for 2 minutes, and irradiated with UV lights for 6 to 12 seconds at the output of 60% by using a D bulb (lamp, 90 mW/cm) manufactured by Fusion UV Inc. at 30° C. to prepare an acryl layer. The coating solution A-1 shown in Table 1 was applied on this acryl layer at room temperature so that a thickness of a dried film after drying becomes 5 µm. After drying the coating layer at room temperature for 30 seconds, the coating layer was heated in the atmosphere at 85° C. for 2 minutes, and irradiated with UV lights for 6 to 12 seconds at the output of 60% by using a D bulb (lamp, 90 mW/cm) manufactured by Fusion UV Inc. at 30° C. to prepare a liquid crystal layer. The coating solution A-2 shown in Table 1 was applied on this liquid crystal layer at room temperature so that a thickness of a dried film after drying becomes 5 µm. After drying the coating layer at room temperature for 30 seconds, the coating layer was heated in the atmosphere at 85° C. for 2 minutes, and irradiated with UV lights for 6 to 12 seconds at the output of 60% by using a D bulb (lamp, 90 mW/cm) manufactured by Fusion UV Inc. at 30° C. to prepare a liquid crystal layer. The coating solution A-3 shown in Table 1 was further applied on this liquid crystal layer at room temperature so that a thickness of a dried film after drying becomes 5 µm. After drying the coating layer at room temperature for 30 seconds, the coating layer was heated in the atmosphere at 85° C. for 2 minutes, and irradiated with UV lights for 6 to 12 seconds at the output of 60% by using a D bulb (lamp, 90 mW/cm) manufactured by Fusion UV Inc. at 30° C. to prepare a reflection film SC-1.

Preparation of Reflection Film SC-2 to SC-6 (Scattering Type)

Reflection films SC-2 to SC-6 were prepared in the same manner as in the preparation of the reflection film SC-1, except that three coating solutions shown below were respectively used, instead of the coating solutions A-1 to A-3.

SC-2: B-1 to B-3
SC-3: A-4 to A-6
SC-4: B-4 to B-6
SC-5: A-3, A-7, and A-8
SC-6: B-3, B-7, and B-8

TABLE 1

| | | Coating solution (A) | | | | | | | |
|---|---|---|---|---|---|---|---|---|---|
| Material (kind) | Material name (manufacturer) | Coating solution A-1 | Coating solution A-2 | Coating solution A-3 | Coating solution A-4 | Coating solution A-5 | Coating solution A-6 | Coating solution A-7 | Coating solution A-8 |
| Liquid crystal compound | Compound 1 | 100 parts by mass | 100 parts by mass | 100 parts by mass | 100 parts by mass | 100 parts by mass | 100 parts by mass | 100 parts by mass | 100 parts by mass |
| Polymerization initiator | Irg-819(BASF) | 4 parts by mass | 4 parts by mass | 4 parts by mass | 4 parts by mass | 4 parts by mass | 4 parts by mass | 4 parts by mass | 4 parts by mass |
| Orientation controlling agent | Compound 2 | 0.03 parts by mass | 0.01 parts by mass | 0.01 parts by mass | 0.03 parts by mass | 0.01 parts by mass | 0.01 parts by mass | 0.01 parts by mass | 0.01 parts by mass |
| Chiral agent | LC-756(BASF) | 3.24 parts by mass | 2.99 parts by mass | 2.78 parts by mass | 7.13 parts by mass | 6.45 parts by mass | 5.89 parts by mass | 2.67 parts by mass | 2.48 parts by mass |
| Solvent | 2-butanone (Wako Pure Chemical Industries, Ltd.) | Suitably adjusted in accordance with film thickness | Suitably adjusted in accordance with film thickness | Suitably adjusted in accordance with film thickness | Suitably adjusted in accordance with film thickness | Suitably adjusted in accordance with film thickness | Suitably adjusted in accordance with film thickness | Suitably adjusted in accordance with film thickness | Suitably adjusted in accordance with film thickness |
| | | Coating solution (B) | | | | | | | |
| Material (kind) | Material name (manufacturer) | Coating solution B-1 | Coating solution B-2 | Coating solution B-3 | Coating solution B-4 | Coating solution B-5 | Coating solution B-6 | Coating solution B-7 | Coating solution B-8 |
| Liquid crystal compound | Compound 1 | 100 parts by mass | 100 parts by mass | 100 parts by mass | 100 parts by mass | 100 parts by mass | 100 parts by mass | 100 parts by mass | 100 parts by mass |
| Polymerization initiator | Irg-819(BASF) | 4 parts by mass | 4 parts by mass | 4 parts by mass | 4 parts by mass | 4 parts by mass | 4 parts by mass | 4 parts by mass | 4 parts by mass |
| Orientation controlling agent | Compound 2 | 0.03 parts by mass | 0.01 parts by mass | 0.01 parts by mass | 0.03 parts by mass | 0.01 parts by mass | 0.01 parts by mass | 0.01 parts by mass | 0.01 parts by mass |
| Chiral agent | Compound 3 | 5.26 parts by mass | 4.85 parts by mass | 4.50 parts by mass | 11.86 parts by mass | 10.70 parts by mass | 9.74 parts by mass | 4.50 parts by mass | 4.18 parts by mass |
| Solvent | 2-butanone (Wako Pure Chemical Industries, Ltd.) | Suitably adjusted in accordance with film thickness | Suitably adjusted in accordance with film thickness | Suitably adjusted in accordance with film thickness | Suitably adjusted in accordance with film thickness | Suitably adjusted in accordance with film thickness | Suitably adjusted in accordance with film thickness | Suitably adjusted in accordance with film thickness | Suitably adjusted in accordance with film thickness |

| | Coating solution (C) acryl treatment | |
|---|---|---|
| Material (kind) | Material name (manufacturer) | Coating solution C |
| Acryl | Viscoat 360 (manufactured by Osaka Organic Chemical Industry Ltd.) | 100 parts by mass |
| Polymerization initiator | Irg-819(BASF) | 4 parts by mass |
| Surfactant | Compound 2 | 0.03 parts by mass |
| Solvent | 2-butanone (Wako Pure Chemical Industries, Ltd.) | Suitably adjusted in accordance with film thickness |

TABLE 1-continued

Compound 1

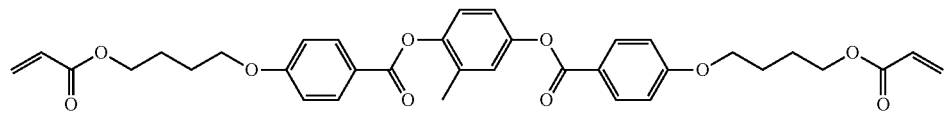 [SMILES: C=CC(=O)OCCCCOc1ccc(C(=O)Oc2ccc(OC(=O)c3ccc(OCCCCOC(=O)C=C)cc3)c(C)c2)cc1]

Compound 2: compound disclosed in JP2005-99248A

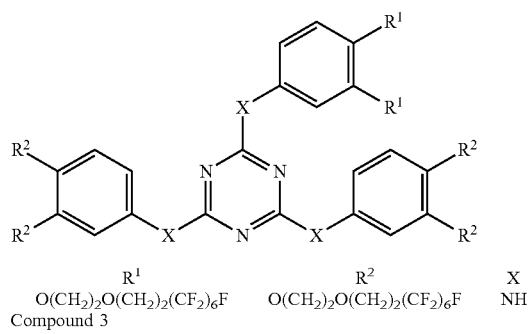

| R¹ | R² | X |
|---|---|---|
| O(CH$_2$)$_2$O(CH$_2$)$_2$(CF$_2$)$_6$F | O(CH$_2$)$_2$O(CH$_2$)$_2$(CF$_2$)$_6$F | NH |

Compound 3

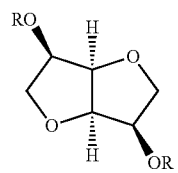

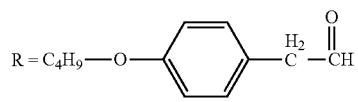

Preparation of Circularly Polarized Light Separation Films a1 to a10

The prepared reflection films MR-1 to MR-6 and the reflection films SC-1 to SC-6 were bonded to each other or the films are used alone, as shown in Table 2, to prepare circularly polarized light separation films a1 to a10. In a case of bonding the MR film and the SC film prepared as described above to each other, the bonding was performed with the following procedure.
A UV curable adhesive Exp. U12034-6 manufactured by DIC Corporation was applied to a surface of a reflection film of a lower layer shown in Table 2 on a liquid crystal layer side by using a wire bar at room temperature so that a thickness of a dried film after drying becomes 5 μm. This coated surface and a surface of a reflection film of an upper layer shown in Table 2 on the liquid crystal layer side were bonded to each other so that air bubbles were not generated, and were UV-irradiated using a D bulb (lamp 90 mW/cm) manufactured by Fusion UV Inc., for 6 to 12 seconds with output of 60% at 30° C. Then, the PET film which was the support of the upper layer was peeled off.

Preparation of Circularly Polarized Light Separation Films a11 and a12 a11 was prepared by performing the bonding by shifting an angle of a γ/4 plate and an optical axis of a linear polarizing plate by 45°, and a12 was prepared by performing the bonding by shifting an angle of a λ/4 plate and an optical axis of a linear polarizing plate by −45°. As the λ/4 plate, ¼λ, of 700 to 1,000 nm of an achromatic wavelength plate (phase difference plate) manufactured by Edmund Optics Japan was used. As the linear polarizing plate, a high contrast polarizing filter for NIR manufactured by Edmund Optics Japan was used.

The bonding of the λ/4 plate and the linear polarizing plate was performed in the same manner as the bonding of the MR films and the SC films described above, by using a UV curable adhesive Exp. U12034-6 manufactured by DIC Corporation.

Preparation of Linearly Polarized Light Separation Layers b1 and b2

As a linearly polarized light separation layer b1, the high contrast polarizing filter for NIR manufactured by Edmund Optics Japan which is the linear polarizing plate used as described above was used.

As a linearly polarized light separation layer b2, a polarizing filter for near infrared light manufactured by Edmund Optics Japan which is the linear polarizing plate was used.

TABLE 2

|  | Circularly polarized light separation film a1 | Circularly polarized light separation film a2 | Circularly polarized light separation film a3 | Circularly polarized light separation film a4 | Circularly polarized light separation film a5 |
|---|---|---|---|---|---|
| Upper layer | MR-1 | MR-1 | MR-2 | MR-2 | MR-3 |
| Lower layer | Not present | SC-1 | Not present | SC-2 | Not present |

|  | Circularly polarized light separation film a6 | Circularly polarized light separation film a7 | Circularly polarized light separation film a8 | Circularly polarized light separation film a9 | Circularly polarized light separation film a10 |
|---|---|---|---|---|---|
| Upper layer | MR-3 | MR-4 | MR-4 | MR-5 | MR-6 |
| Lower layer | SC-3 | Not present | SC-4 | SC-5 | SC-6 |

|  | Circularly polarized light separation film a11 | Circularly polarized light separation film a12 | Circularly polarized light separation film b1 | Circularly polarized light separation film b2 |
|---|---|---|---|---|
| Upper layer | λ/4 plate | λ/4 plate | Linear polarizing plate | Linear polarizing plate |
| Lower layer | Linear polarizing plate | Linear polarizing plate | Not present | Not present |

Examples 1 to 6 and Comparative Examples 1 to 10

Figure 2A:
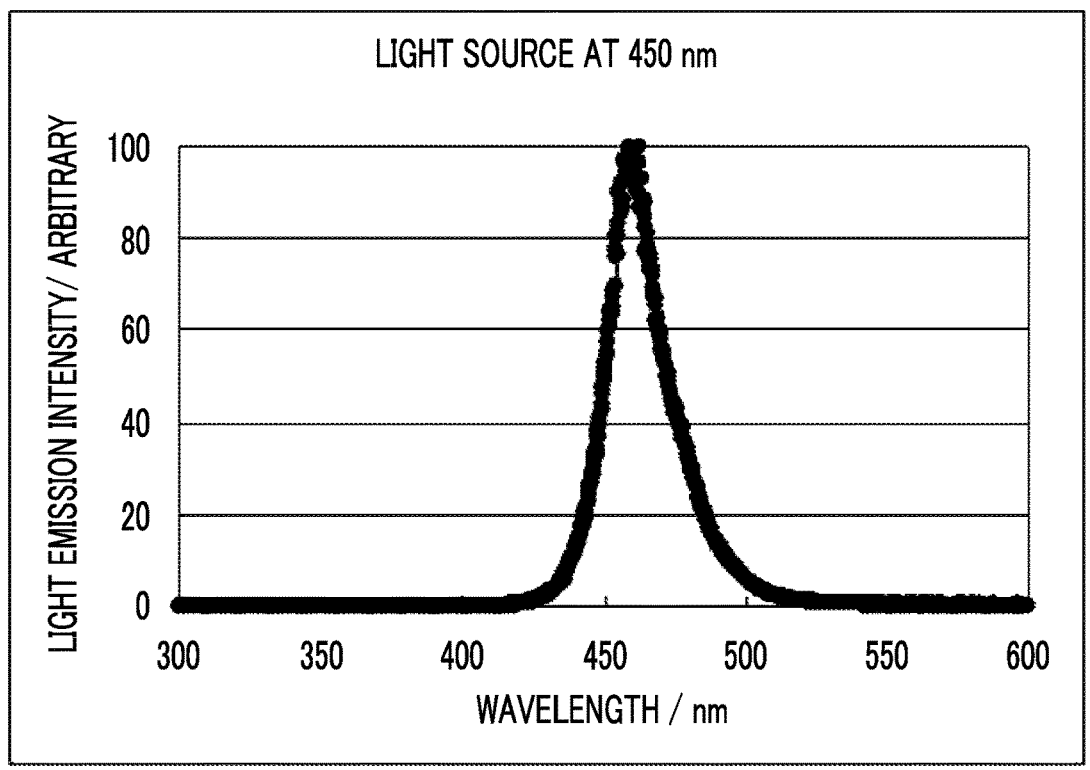
FIGS. 2A and 2B are views showing emission spectra of a light source used in examples.
Figure 2B:
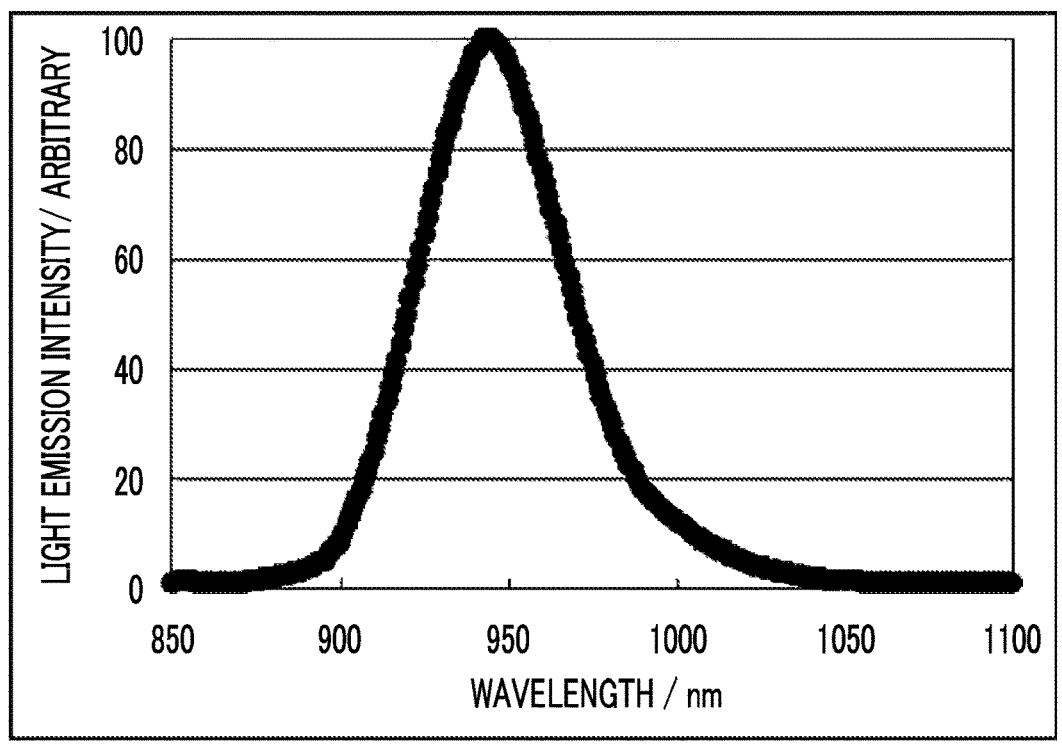

The prepared circularly polarized light separation films a1 to a12 and the linearly polarized light separation films b1 and b2 were combined with each other in the emission unit and the detection unit as shown in Table 3, and the sample sensing was performed. As the light source, an LED having the center wavelength of light emission intensity at light emitting spectra of 450 nm or 940 nm shown in FIGS. 2A and 2B was used, as the light receiving element (light detector), a light power meter ML9001A manufactured by Anritsu Corporation was used, and as a sample, a TAC film having Re of approximately 0 nm and Rth of approximately 100 nm was used.

The light source, the light detector, and the circularly polarized light separation film were disposed in the arrangement A or B of FIG. 1A or FIG. 1B, as shown in Table 3. The sample was disposed so as to have a short side direction of the sample plane in the plane of the drawing of the target object movement unit shown in FIG. 1 and a long side direction of the sample plane in a depth direction of the drawing, and the sample was set to be present on the intersection between the light path and the target object movement unit at the time of the sensing.

In a case of installing the circularly polarized light separation films a1 to a12 and the linearly polarized light separation films b1 and b2 in the light source, the lower layer side shown in Table 2 was set to become the light source side, and in a case of installing the circularly polarized light separation films and the linearly polarized light separation films in the light detector, the lower layer side shown in Table 2 was set to become the light detector side. The tilt angle and the wavelength of the light source were selected as shown in Table 3.

The output of the light detector in a case where the sample is installed and a case where no sample is present is shown in Table 3. Table 3 shows a value in a case where the output of the detector in a state where the circularly polarized light separation films or the linearly polarized light separation films are is installed in neither of the light source and the detector is 100. A ratio of a measured value in a case where the sample is present with respect to a measured value in a case where the sample is not present, is expressed as "sample present/no sample" and displayed as a percentage. As this ratio is greater than 100%, it is considered that the erroneous sensing hardly occurs.

For the films prepared in Examples and Comparative Examples, moisture-heat durability was evaluated based on the following criteria. The results are shown in Table 3.

A: Amount of change in output of a light detector in a case where a sample is not present, after leaving at 85° C. and humidity of 85% for 100 hours is less than 0.5

B: The amount of change is equal to or greater than 0.5 and less than 1.0

C: The amount of change is equal to or greater than 1.0

TABLE 3

|  | Light source light emitting wavelength | Polarizing filter Light source side | Polarizing filter Light receiving side | Film arrangement position relationship | Film arrangement | Sample tilt angle | Output of light detector No sample | Output of light detector Sample present | Moisture-heat durability | Sample present/no sample [%] |
|---|---|---|---|---|---|---|---|---|---|---|
| Example 1 | 940 nm | a1 | a3 | — | A | 60 degrees | 0.81 | 3.25 | A | 401.2 |
| Example 2 | 940 nm | a2 | a4 | — | A | 60 degrees | 0.14 | 4.09 | A | 2921.4 |
| Example 3 | 450 nm | a5 | a7 | — | A | 35 degrees | 0.81 | 3.25 | A | 401.2 |
| Example 4 | 450 nm | a6 | a8 | — | A | 35 degrees | 0.14 | 4.09 | A | 2921.4 |
| Example 5 | 940 nm | a9 | a10 | — | B | 60 degrees | 0.16 | 3.87 | A | 2418.8 |
| Example 6 | 940 nm | a11 | a12 | — | A | 60 degrees | 0.09 | 2.40 | B | 2666.7 |

TABLE 3-continued

| | Light source light emitting wavelength | Polarizing filter Light source side | Polarizing filter Light receiving side | Film arrangement position relationship | Film arrangement | Sample tilt angle | Output of light detector No sample | Output of light detector Sample present | Moisture-heat durability | Sample present/no sample [%] |
|---|---|---|---|---|---|---|---|---|---|---|
| Comparative Example 1 | 940 nm | a1 | a3 | — | A | 0 degrees | 0.81 | 0.89 | A | 109.9 |
| Comparative Example 2 | 940 nm | a2 | a4 | — | A | 0 degrees | 0.14 | 0.22 | A | 157.1 |
| Comparative Example 3 | 940 nm | a2 | a4 | — | A | 15 degrees | 0.14 | 0.27 | A | 192.9 |
| Comparative Example 4 | 450 nm | a5 | a7 | — | A | 0 degrees | 0.81 | 0.89 | A | 109.9 |
| Comparative Example 5 | 450 nm | a6 | a8 | — | A | 0 degrees | 0.14 | 0.22 | A | 157.1 |
| Comparative Example 6 | 940 nm | a11 | a12 | — | A | 0 degrees | 0.09 | 0.12 | B | 133.3 |
| Comparative Example 7 | 940 nm | b1 | b1 | crossed Nicol | A | 0 degrees | 0.00 | 0.00 | C | — |
| Comparative Example 8 | 940 nm | b1 | b1 | crossed Nicol | A | 60 degrees | 0.00 | 1.11 | C | — |
| Comparative Example 9 | 940 nm | b2 | b2 | crossed Nicol | A | 0 degrees | 0.73 | 0.66 | C | 90.4 |
| Comparative Example 10 | 940 nm | b2 | b2 | crossed Nicol | A | 60 degrees | 0.73 | 0.64 | C | 87.7 |

In all of Examples 1 to 6, the measured value in a case where a sample was present was equal to or greater than 200% of the measured value in a case where a sample was not present, and a difference in light intensity with which the erroneous sensing hardly occurs, was obtained. On the other hand, in Comparative Examples 1 to 7 in which the tilt angle was 0°, the measured value in a case where a sample was present was less than 200% of the measured value in a case where a sample was not present. In the examples in which the linearly polarized light separation film b1 was used, high output was obtained in the example in which the sample tilt angle was 60°, but output of the light detector was not obtained under the conditions without a sample. This means that an opaque product cannot be sensed. In the examples in which the linearly polarized light separation film b2 was used, a difference between the measured value in a case where a sample was present and the measured value in a case where a sample was not present is small, and thus, it is considered that the erroneous sensing occurs, in a case where the sensing was performed by using the sensing method. In addition, in the examples in which the linearly polarized light separation film b2 was used, the measured value in a case where a sample was present is smaller than the measured value in a case where a sample was not present, and this may be due to a low degree of polarization of the linear polarizing plate.

Regarding the moisture-heat durability, a performance deterioration was greatly observed only in the linear polarizing plate (C), but the moisture-heat durability was improved in a state where the λ/4 layer was bonded to the linear polarizing plate (Example 6). It is considered that the λ/4 layer and the adhesive layer functioned as a barrier with respect to humidity or the like.

Examples 7 to 9

Measurement was performed by using a TAC film having Re of approximately 25 nm and Rth of approximately 100 nm as a sample and by using the light source and the light receiving element which were the same as those in Example 1. The measurement was performed in the arrangement A of FIG. 1A, the tilt angle was 60°, and the measurement wavelength was 940 nm. The prepared circularly polarized light separation film a2 was used on the light source side and the circularly polarized light separation film a4 was used on the light receiving side. The lower layer side of the circularly polarized light separation film a2 shown in Table 2 was set to be the light source side, and the lower layer side of the circularly polarized light separation film a4 shown in Table 2 was set to be the light detector side.

Figure 3:
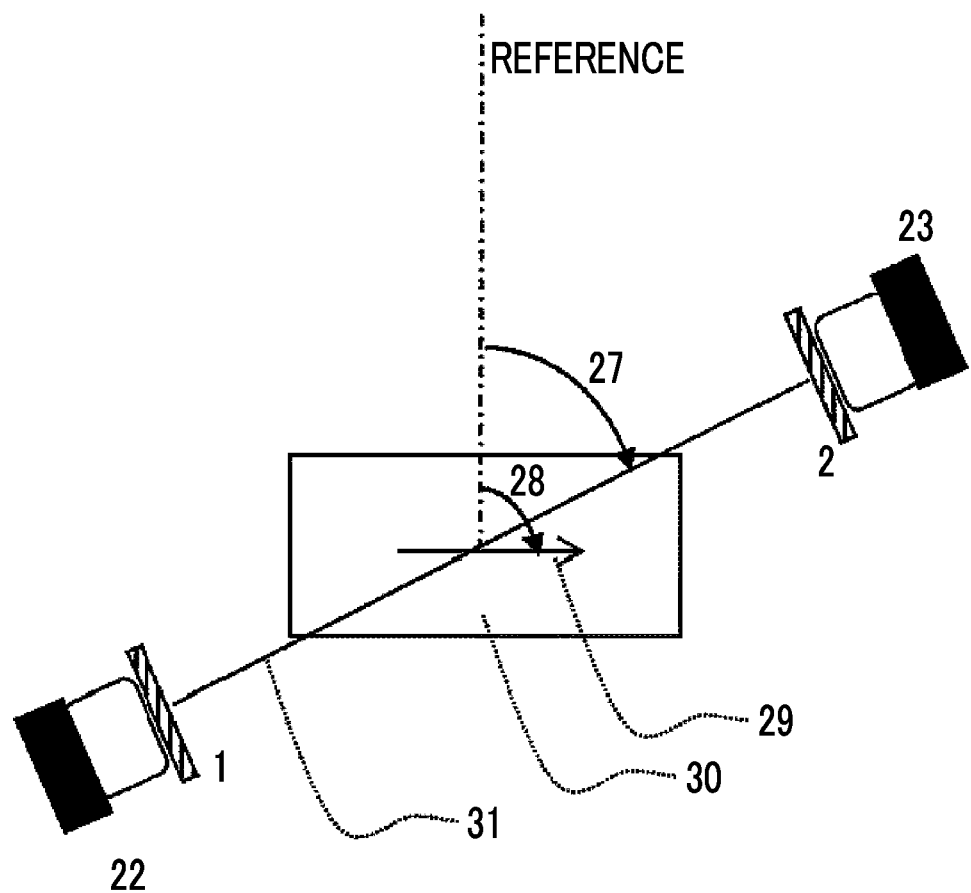
FIG. 3 is a diagram explaining a sensor in-plane angle and a slow axis in-plane angle of Examples 7 to 9, and is a schematic view of a system observed in a normal direction of a sample.

In a case where one direction in the normal direction of the sample was set as 0° as a reference, the light source and the light receiving element were disposed so that an angle of the plane of incidence of the emitted light of the light source (sensor in-plane angle: see FIG. 3) becomes 0°, 60°, 90°, or 120°. At this time, the output of the light detector in a case where the sample was set so that the direction in a normal direction of the sample of the slow axis of the sample (slow axis in-plane angle: see FIG. 3) was set to be 0°, 45°, or 90°, by using the direction described above as a reference, in the same manner as described above, and the value of "sample present/no sample" was obtained in the same manner as described above, by comparing to the output of the light detector in a case where a sample is not present. The results are shown in Table 4.

As shown in Table 5, in the detection where the sensor in-plane angle is 0°, in a case where the slow axis of the sample was provided at 0°, 45°, and 90°, the sensitivity in which the value described above is at least 330.1% was obtained. Meanwhile, in a case where three kinds of detection in which the sensor in-plane angles were 0° and 90° was performed and the detection having a great value of a signal was used, the sensitivity in which the value described above is at least 6784.5% was obtained. In addition, in a case where two kinds of detection in which the sensor in-plane angles were 0°, 60°, and 120° was performed and the detection having a great value of a signal was used, the sensitivity in which the value described above is at least 10097.5% was obtained, and the sensing sensitivity was remarkably improved.

TABLE 4

| | Sample present/no sample [%] | | | |
|---|---|---|---|---|
| | | Slow axis in-plane angle | | |
| | | 0 | 45 | 90 |
| Sensor in-plane angle | 0 | 14066.9 | 6784.5 | 330.1 |
| | 60 | 3204.3 | 12866.3 | 10097.5 |
| | 90 | 330.1 | 6784.5 | 14066.9 |
| | 120 | 3204.3 | 1326.0 | 10097.5 |

TABLE 5

| | Sensor in-plane angle | Sample present/no sample [%] |
|---|---|---|
| Example 7 | 0° | 330.1 |
| Example 8 | 0°, 90° | 6784.5 |
| Example 9 | 0°, 60°, 90° | 10097.5 |

EXPLANATION OF REFERENCES

1: circularly polarized light separation film 1
2: circularly polarized light separation film 2
11: circularly polarized light separation film 11
12: circularly polarized light separation film 12
16: mirror reflection member
17: attachment
22: light source
23: light receiving element
24: target object movement unit
25: light path
26: tilt angle
27: sensor in-plane angle
28: slow axis in-plane angle
29: slow axis of sample
30: sample (observed in normal direction)
31: plane of incidence of emitted light

What is claimed is:

1. A method of sensing a target object, comprising:
sensing the target object by sensing light that is derived from emitted light and has passed through the target object,
wherein the emitted light is circularly polarized light,
the sensed light is circularly polarized light,
the target object is a transparent product,
the light derived from the emitted light is incident to the target object at an angle greater than 20° and equal to or smaller than 70° that is formed with a normal line of the target object, and
two or more emitted light rays having planes of incidence different from each other are used as the emitted light.

2. The method according to claim 1,
wherein the sensing is direct sensing of light which is the emitted light which has passed through the target object, and
a sense of circularly polarized light of the emitted light is opposite to a sense of circularly polarized light of the sensed light.

3. The method according to claim 1,
wherein three emitted light rays having planes of incidence different frons each other are used as the emitted light.

4. The method according to claim 1,
wherein the sensing is sensing of reflected light of light derived from the emitted light, and
a sense of circularly polarized light of the emitted light is the same as a sense of circularly polarized light of the sensed light.

5. The method according to claim 4,
wherein the sensing is sensing of reflected light which has passed through the target object again, after the emitted light passes through the target object and is reflected.

6. The method according to claim 1,
wherein the planes of incidence different from each other form an angle of 10° to 90°.

7. The method according to claim 6,
wherein three emitted light rays having planes of incidence different from each other are used as the emitted light.

8. A system which senses a target object comprising:
light source with a circularly polarized light separation film, which selectively emits circularly polarized light;
position where a target object to be sensed is disposed; and
light detector with a circularly polarized light separation film, which selectively senses circularly polarized light, in a light path of the circularly polarized light in this order,
wherein a sense of circularly polarized light selectively emitted by the light source is opposite to a sense of circularly polarized light selectively sensed by the light detector,
a light path of light where light derived from the emitted light from the light source is incident to the light detector intersects with the position where the target object to be sensed is disposed in an intersection portion,
an angle formed by the light path and a normal line of the position where the target object to be sensed is disposed in the intersection portion is greater than 20° and equal to or smaller than 70°,
two or more light sources with emitted light rays having planes of incidence different from each other are used as the light source, and
the light detector is disposed in each of planes of incidence.

9. The system according to claim 8,
wherein the target object is a transparent product.

10. The system according to claim 8,
wherein the light source is equipped with the circularly polarized light separation film (1),
the light detector is equipped with the circularly polarized light separation film (2),
the light source, the circularly polarized light separation film (1), the position where the target object to be sensed is disposed, the circularly polarized light separation film (2), and the light detector are disposed in the light path of the circularly polarized light in this order, and
the circularly polarized light separation film (1) and the circularly polarized light separation film (2) allow selective transmission of circularly polarized light rays having senses opposite to each other.

11. The system according to claim 10,
wherein both of the circularly polarized light separation film (1) and the circularly polarized light separation film (2) are films including circularly polarized light separation layers obtained by fixing a cholesteric liquid-crystalline phase.

* * * * *